(12) United States Patent
Abe et al.

(10) Patent No.: US 7,466,236 B2
(45) Date of Patent: Dec. 16, 2008

(54) DEVICE FOR JUDGING TYPES OF LIQUID IN CONTAINER AND CONTROL METHOD THEREFOR

(75) Inventors: Takeshi Abe, Tokyo (JP); Yasuhiko Shinozawa, Tokyo (JP); Tomohide Machida, Tokyo (JP); Kouichiro Yamada, Tokyo (JP)

(73) Assignee: Tokyo Gas Co., Ltd., Tokyo (JP)

( * ) Notice: Subject to any disclaimer, the term of this patent is extended or adjusted under 35 U.S.C. 154(b) by 469 days.

(21) Appl. No.: 10/564,472

(22) PCT Filed: Jul. 14, 2004

(86) PCT No.: PCT/JP2004/010379

§ 371 (c)(1),
(2), (4) Date: Jan. 13, 2006

(87) PCT Pub. No.: WO2005/008230

PCT Pub. Date: Jan. 27, 2005

(65) Prior Publication Data

US 2006/0201234 A1    Sep. 14, 2006

(30) Foreign Application Priority Data

Jul. 16, 2003 (JP) .............................. 2003-198046
Nov. 14, 2003 (JP) .............................. 2003-385627

(51) Int. Cl.
*G08B 21/00* (2006.01)

(52) U.S. Cl. .................... 340/620; 340/592; 340/693.9; 73/53.01; 73/53.04; 73/54.02; 73/64.56; 73/335.04

(58) Field of Classification Search .............. 340/545.4, 340/620; 73/53.04, 54.02, 335.04, 64.56
See application file for complete search history.

(56) References Cited

U.S. PATENT DOCUMENTS 2,285,152 A * 6/1942 Firestone ..................... 324/671

(Continued)

FOREIGN PATENT DOCUMENTS

JP    7-174726    7/1995

(Continued)

*Primary Examiner*—George A Bugg
*Assistant Examiner*—Son M Tang
(74) *Attorney, Agent, or Firm*—Westerman, Hattori, Daniels & Adrian, LLP.

(57) ABSTRACT

[Theme] To provide a device or a judging method for judging the type of liquid inside a container that can be applied to containers of various shapes and can be applied to cases where the remaining amounts of liquids in containers differ. [Solution Means] This invention's device for judging the type of liquid inside a container is equipped with: a plate capacitor 1, wherein two plate electrodes 1a and 1b are positioned in opposing manner; a container supporting member 3, holding, in a region besides the region sandwiched between plate electrodes 1a and 1b, a non-conductive container 2 that can contain a liquid in its interior; an oscillation circuit 4, containing capacitor 1; and a control part 5, detecting the oscillation frequency of the oscillation circuit; and container supporting member 3 is arranged to adjust the distance from plate electrode 1a to container 2 in accordance with the size of container 2. Also, a third electrode 18, of the same electric potential as plate electrode 1b, is disposed in contact with a bottom part of container 2.

22 Claims, 15 Drawing Sheets

U.S. PATENT DOCUMENTS

| | | | |
|---|---|---|---|
| 2,833,147 A * | 5/1958 | Di Franco | 73/304 C |
| 4,358,423 A * | 11/1982 | Nedetzky | 422/82.02 |
| 5,135,485 A * | 8/1992 | Cohen et al. | 604/67 |
| 5,269,175 A * | 12/1993 | Chmiel et al. | 73/53.05 |
| 5,497,102 A * | 3/1996 | Burrows et al. | 324/663 |
| 6,857,313 B2 * | 2/2005 | Williamson | 73/304 C |
| 7,021,122 B1 * | 4/2006 | Rosemberg et al. | 73/54.01 |
| 7,107,837 B2 * | 9/2006 | Lauman et al. | 73/304 C |

FOREIGN PATENT DOCUMENTS

| | | |
|---|---|---|
| JP | 2946842 | 7/1999 |
| JP | 2000-65775 | 3/2000 |
| JP | 2001-66273 | 3/2001 |
| JP | 2002-191252 | 7/2002 |

* cited by examiner

Without electrode

DEVICE FOR JUDGING TYPES OF LIQUID IN CONTAINER AND CONTROL METHOD THEREFOR

TECHNICAL FIELD

This invention relates to a device for judging the type of liquid inside a container and a control method for the same and is particularly effective in application to an art of judging whether or not a liquid inside a container is a non-hazardous liquid having water as a main component.

BACKGROUND ART

With airplanes, trains, buses, and other forms of passenger transportation, there is an obligation to transport the passengers safely. Especially with airplanes, since accidents thereof are enormous in damage, a high degree of caution must be paid for safety. Passengers using airplanes are thus subject to baggage inspection using an X-ray image taking device, body inspection using a metal detector or by body check, and, if necessary, questioning etc., in order to distinguish passengers with malicious intent and deny the use of an airplane to such passengers. However, in view of the large number of passengers and convenience to passengers, it is difficult to carry out strict inspections and questioning, which take a large amount of time, on all passengers. Meanwhile a passenger with malicious intent (such as a terrorist) will try to get past such inspections and bring a hazardous object inside a plane. Though problems will not occur in particular in regard to hazardous objects that can be discovered by currently used means of baggage inspection, etc., hazardous objects that cannot be detected by a metal detector or X-ray image taking, such as gasoline and other flammable liquids, etc., are comparatively difficult to detect. Gasoline and other hazardous liquids can be procured readily in the market, and when such a hazardous liquid is filled in a container (for example a PET bottle) for a commercially sold drink, it becomes difficult to distinguish between a true drink, and such an act can said to be a dangerous act that can readily be employed by a person with malicious intent. Countermeasures against such dangerous acts must thus be considered adequately.

For distinguishing between a hazardous liquid, such as gasoline, etc., and a drink having water as a main component, there are various distinguishing methods, such as sensory inspection methods, wherein the odor is smelled, etc. However, since rapidity of inspection is required of baggage inspection in using a plane, it is preferable for an inspection to be carried out rapidly in a non-contacting manner. As rapid, non-contacting inspection methods, there are methods that make use of differences in the dielectric constants of liquids. Whereas water is high in dielectric constant, gasoline and other hazardous liquids are generally low in dielectric constant. Such dielectric constant differences may thus be considered for use in judging the type of liquid.

In Patent Document 1 is disclosed a method and device for judging the type of liquid from the exterior of a container. With the art described in this document, the interior of a container is filled with a liquid, a pair of electrodes are positioned outside the container so as to sandwich at least a part of the liquid, and the capacitance of a capacitor formed by these electrodes is measured to judge the type of the liquid. In using such an art, the capacitance in the case where the liquid is water and the capacitance in the case where the liquid is a hazardous liquid (for example, gasoline) are measured in advance, and by then positioning a container filled with a liquid of unknown content between the electrodes and measuring the capacitance in this state, the type of liquid inside the container can be judged instantly and accurately.

Patent Document 1 Japanese Published Unexamined Patent Application No. 2001-272368

DISCLOSURE OF THE INVENTION

However, the liquid type judging method of the art of the abovementioned Patent Document 1 has the following problems. Firstly, the size of the container and the amount of liquid in the container must be fixed. As is well known, when a dielectric body is inserted between the electrodes of a capacitor, the capacitance value changes in accordance with the dielectric constant. Though the art of Patent Document 1 indeed uses this principle, the capacitance also changes if the shape (width or thickness) or positioning of the dielectric body is changed. Thus if the dielectric constant of a dielectric body that is inserted between the electrodes of a capacitor is to be made known from the measurement of the capacitance, the shape and positioning of the dielectric body must be fixed. With the art of Patent Document 1, this means that the shape and positioning of the container and the amount of liquid filled in the container must be fixed. Thus when the art of this document is applied to an airplane baggage inspection, such as that described above, there will be difficulties in principle. That is, drinks that are brought by passengers are put in PET bottles of various shapes and the remaining amounts also differ and are not fixed. The art described in the referenced document can thus be used under extremely limited conditions (for example, in a case where the electrodes are positioned to match a PET bottle, etc., of specific shape) and cannot be used in inspections accommodating for the shapes of various containers nor inspections for cases where the remaining amounts of liquids in containers differ.

An object of this invention is to provide a device and a judging method for judging the type of liquid inside a container that can be applied to containers of various shapes and can be applied to cases where the remaining amounts of liquids in containers differ. In particular, an object of this invention is to provide a device that can judge the type of liquid with good sensitivity even when the remaining amount of the liquid in a container is low.

The invention disclosed in this Description is as follows. That is, a device for judging the type of liquid inside a container of a first aspect of the invention of this Application comprises: a plate capacitor, having two plate electrodes positioned in opposing manner; and a container supporting means, holding, in a region besides the region sandwiched by the abovementioned two plate electrodes, a non-conductive container that can contain a liquid in the interior thereof; and judges the type of liquid inside the container by detecting the capacitance of the abovementioned capacitor or the oscillation frequency of an oscillation circuit containing the abovementioned capacitor.

A device for judging the type of liquid inside a container of another aspect (second aspect) of the invention of this Description comprises: a plate capacitor, having two plate electrodes positioned in opposing manner; a container supporting means, holding, in a region besides the region sandwiched by the abovementioned two plate electrodes, a non-conductive container that can contain a liquid in the interior thereof; and a third electrode, besides the abovementioned two plate electrodes, that is an electrode outside the abovementioned container and is set along a portion of the abovementioned container at which the abovementioned liquid inside the abovementioned container is retained due to gravity; and judges the type of liquid inside the container by detecting the capacitance of the abovementioned capacitor or the oscillation frequency of an oscillation circuit containing the abovementioned capacitor.

With the devices for judging the type of liquid in a container of the first and second aspects of this invention, a container is not positioned between the electrodes of a capacitor but is positioned outside the electrodes. The amount of change of the capacitance of the capacitor resulting from the positioning of a container containing a liquid will thus be small in comparison to the case where the container is positioned between the electrodes. However in comparison to the case where the container is positioned between the electrodes, the proportion of change of the capacitance due to a change of the container shape and a difference in the amount of liquid inside a container can be made relatively small. This is because, the present invention does not use the electric field between the electrodes of the capacitor (that is, the parallel electric field region, which is the region at which the electric field strength is the greatest) for detecting a change in capacitance but uses a leakage electric field (which is lower in electric field strength than the parallel electric field region) that leaks from between the electrodes of the capacitor. Since a leakage electric field is generally a divergent field, the electric field strength becomes weaker the further away from the capacitor. By devising the positioning of a container (for example, by positioning a container so that the larger the container, the further away it is from the capacitor) and, since a liquid remaining inside a container collects at the bottom of the container, by positioning the capacitor at a lower side of the container, the proportion of change of capacitance due to container shape and remaining amount of liquid in a container can be dulled comparatively. In other words, the dependence of the number of electric flux lines, passing through the liquid to be detected, on the container shape and remaining liquid amount can be lessened as much as possible. By such arrangements, this invention enables rapid and accurate judgment of the type of liquid in a container even when the container shape and the amount of liquid remaining in the container varies.

Furthermore, the second aspect of this invention has a third electrode in addition to the two plate electrodes that form the capacitor. This third electrode is positioned at an outer side of a container along a portion of the container at which a liquid in the container is retained due to gravity, and has a function of drawing the leakage electric field from the capacitor in the direction of the liquid in the container. Here, the "portion of the container at which a liquid in the container is retained due to gravity" is, for example, in the case where the container is set with its side down or inclined on a level surface and the capacitor is positioned along the level surface or the inclined surface, the portion corresponding to the bottom surface or a side surface (not the side surface at which the capacitor is positioned) of the container. In the case where the container is positioned upright, a side surface at a bottom part of the container corresponds to being the abovementioned portion. By positioning such a third electrode, the leakage electric field from the capacitor can be drawn towards the container's bottom part in the gravity direction (the portion at which the liquid in the container stays) and the change of capacitance of the capacitor according to the type of liquid in the container can be detected as a large change, that is, improvement of the precision of judgment of the liquid type can be realized.

The abovementioned third electrode may be a plate electrode or a line electrode, which is positioned along a surface that is a flat surface perpendicular to the abovementioned plate capacitor and contacts an outer side of the abovementioned container. Though the position and shape of the third electrode may be arbitrary as long as it is positioned along a portion at which the liquid in the container stays, when the third electrode is a plate electrode that is set along a flat surface that is perpendicular to the plate capacitor, an electrode arrangement that is suited for the shapes of PET bottles, which are assumed as the containers, can be realized. The electrode shape does not have to be plate-like, and a linear electric line (wire) may be used as it is as an electrode.

Also, the third electrode may be arranged to move to an outer surface of the abovementioned container upon detection of the abovementioned container being positioned on the abovementioned container supporting means or in linkage with the abovementioned container being positioned on the abovementioned container supporting means. That is, the third electrode does not have to be fixed and may be arranged to be movable so as to be set along an outer wall of a container upon detection of the positioning of the container or in linkage with the positioning of the container. For example, the positioning of a container on the container supporting means maybe detected with a photoelectric switch, etc., and the third electrode may be driven by a drive means and moved so as to contact an outer wall of the container. Or, a suitable mechanism means may be arranged to actuate when a container is positioned on the container supporting means and the third electrode, which is linked to this mechanism means, may be made to move so as to contact an outer wall of the container. In these cases where the third electrode is moved, the third electrode can be moved so as to contact or become close to an outer wall of a container without dependence on the shape or size of the container.

Also, the voltage of the third electrode may be made to differ in either or both of the absolute value and the phase with respect to the voltage of the capacitor's plate electrode (first plate electrode) that is positioned at the container side or may be made to be equal in voltage to the second plate electrode of the capacitor that opposes the first plate electrode. Normally in order to examine the capacitance or to arrange an oscillation circuit, an AC voltage is applied between the plate electrodes of the capacitor. This AC voltage is applied with one of the electrodes of the capacitor being a reference (normal ground), and with the present invention, the electrode (second plate electrode) at the side far from the container becomes the ground electrode. Here, with this invention the voltage of the third electrode is made to differ in either or both of the absolute value of the amplitude and phase with respect to the first plate electrode. In particular, the voltage (electric potential) of the third electrode is made the same as that (ground potential) of the second plate electrode. By thus setting the potential of the third electrode, the leakage electric field from the capacitor can be drawn towards the liquid inside the container.

Also with the above-described first and second aspects of this invention, the abovementioned container supporting means may be arranged to adjust, in accordance with the size of the abovementioned container, the distance to the abovementioned container from a first plate electrode, which, among the abovementioned two plate electrodes, is positioned at the side of the abovementioned container. With this invention, the container supporting means adjusts the distance from the capacitor to a container in accordance with the size of the container. It thus becomes possible to position a container further away from the capacitor the larger the container so that even when the size of a container changes, the electric flux lines that cross the liquid can be made close to being fixed and the change of dielectric constant of the liquid can be reflected in the change of capacitance.

Specifically, when, with a container having a cylindrical column or rectangular column outer shape, the columnar direction of the container is to be set parallel to the first plate electrode, the container supporting means may be provided with two stairs-like members, which rise in a direction perpendicular to the first plate electrode and the distance between the container and the first plate electrode may be adjusted according to the size of the container by making an outer peripheral surface of the cylindrical column or rectangular column container contact steps or edge parts of steps of the two stairs-like members. Also, a step member may be positioned at one side of the steps that extend in the columnar direction and the outer shape of a container may be put in contact with the steps of the two stairs-like members so that with a larger container, one end thereof will be raised by the step member and the average distance to the first plate electrode will thereby be increased.

In the present Description, the terms "parallel" and "perpendicular" do not mean "parallel" and "perpendicular" in the strict sense. In the strict sense, "perpendicular" or "parallel" means that a plane or a line and another plane or line intersect at an angle of strictly 90 degrees or do not intersect to infinity. However, since when members are actually positioned, there will obviously exist positioning errors and processing errors of the members, deviations (within some range) from an angle of 90 degrees shall be allowed with the present Description. It shall also be deemed that even cases, where an angle between members is intentionally shifted from a perpendicular or parallel state, are included within the scope of "perpendicular" or "parallel" as long as such a case does not fall outside the gist of this invention, that is, the gist that the type of liquid inside a container is measured using a leakage electric field. For example, in the present Description, a case where the positional relationship between members is described as being "perpendicular" shall include the case of strictly 90 degrees as well as a small unintentional or intentional range that includes 90 degrees.

Or, when, with a container having a cylindrical column, rectangular column, or spherical outer shape, the columnar direction of the container is to be set perpendicular to the first plate electrode, the container supporting means may be provided with a structure that is surrounded by stairs-like members, which rise in a direction perpendicular to the first plate electrode, and the distance between the container and the first plate electrode may be adjusted according to the size of the container by making the bottom surface of the rectangular column or cylindrical column container contact steps of the stairs-like members or by making the outer peripheral surface of the spherical shape container contact edge parts of the steps.

Or, when, with a container having a cylindrical column or rectangular column outer shape, the columnar direction of the container is to be set parallel to the first plate electrode, the container supporting means may be provided with a groove, having a V-shaped cross section and an opening in a direction perpendicular to the first plate electrode, and the distance between the container and the first plate electrode may be adjusted according to the size of the container by making an outer peripheral surface of the cylindrical column or rectangular column container contact surfaces of the V-shaped groove.

Or, when, with a container having a cylindrical column, rectangular column, or spherical outer shape, the columnar direction of the cylindrical column or rectangular column is to be set perpendicular to the first plate electrode, the container supporting means may be provided with a conical opening in a direction perpendicular to the first plate electrode, and the distance between the container and the first plate electrode may be adjusted according to the size of the container by making a bottom surface edge part of the rectangular column or cylindrical column container or the outer peripheral surface of the spherical shape container contact wall surfaces of the conical opening.

Needless to say, the change of the liquid dielectric constant may be detected not just by a change of the capacitance of a capacitor but may be detected instead by a change of the oscillation frequency of an oscillation circuit that contains a capacitor.

Also with the above-described invention, the abovementioned container supporting means may be arranged to adjust, in accordance with the size of the abovementioned container, the area of overlap of the abovementioned container with the abovementioned plate electrodes, as projected from the normal direction perpendicular to a first plate electrode, which, among the abovementioned two plate electrodes, is positioned at the side of the abovementioned container. As in the above-described cases of adjusting the distance from the first plate electrode to the abovementioned container, the leakage electric field of a capacitor is used in this case as well. However, the present case differs from the above-described cases, wherein the distance to the container is adjusted, in that the number of electric flux lines crossing a liquid inside a container is made close to being fixed by adjusting the area of overlap of the capacitor and the container. The same effects as those described above can be obtained by this invention as well.

Specifically, when, with a container having a cylindrical column, rectangular column, or spherical outer shape, the columnar direction of the abovementioned cylindrical column or rectangular column is to be set parallel to the abovementioned first plate electrode, the abovementioned container supporting means may be provided with an inclined surface of an acute angle with respect to the abovementioned first plate electrode, and the abovementioned area of overlap of the abovementioned container with the abovementioned plate electrodes may be adjusted according to the size of the abovementioned container by making a bottom edge part of the abovementioned rectangular column or cylindrical column container or the outer peripheral surface of the abovementioned spherical shape container contact the abovementioned inclined surface. Or, when, with a container having a cylindrical column, rectangular column, or spherical outer shape, the columnar direction of the abovementioned cylindrical column or rectangular column is to be set parallel to the first plate electrode, the abovementioned container supporting means may be provided with a stairs-like member, which rises in a direction parallel to the abovementioned first plate electrode, and the abovementioned area of overlap of the abovementioned container with the abovementioned plate electrodes may be adjusted according to the size of the abovementioned container by making the bottom surface of the abovementioned rectangular column or cylindrical column container contact a step of the abovementioned stairs-like member or making the outer peripheral surface of the abovementioned spherical shape container contact an edge part of the abovementioned step.

Also, in the case where a container is to be held parallel to the first plate electrode, the abovementioned container supporting means may be inclined at a predetermined angle with respect to a level surface while maintaining the relative positions of the container and the plate electrodes. This arrangement provides the effect of making a liquid collect at a bottom part of a container without changing the abovementioned distance between the plate electrodes and the container or the area of overlap of the plate electrodes and the container and thus provides the merit of enabling a judgment to be made more accurately when the amount of liquid is low.

The above-described first and second aspects of this invention may further comprise: a sensor, detecting whether or not the abovementioned container is positioned on the abovementioned container supporting means; a means for detecting the amount of change between the capacitance of the abovementioned capacitor or the oscillation frequency of the abovementioned oscillation circuit when the abovementioned container is not positioned on the abovementioned container supporting means and the capacitance of the abovementioned capacitor or the oscillation frequency of the abovementioned oscillation circuit when the abovementioned container is positioned on the abovementioned container supporting means; and a notification means, notifying whether or not the abovementioned change amount is greater than a predetermined threshold value. In this case, the change in the capacitor's capacitance or oscillation frequency before and after the positioning of the container can be measured, and for example, a notification of a normal state can be made in the case where the amount of change is greater than a threshold value (when it can be assumed that the liquid has water as a main component) and a notification of an abnormal state can be made in the case where the amount of change is no more than the threshold value (when it can be at least assumed that the liquid is not water). Display notification by a light emitting element or a display device, acoustic notification by sound, notification by vibration or other form of oscillation, etc., can be cited as examples of the forms of notification.

The above-described first and second aspects of this invention may further comprise: a storage means, recording the capacitance of the abovementioned capacitor or the oscillation frequency of the abovementioned oscillation circuit when the abovementioned container is not positioned on the abovementioned container supporting means; and a means for periodically renewing the abovementioned capacitance or oscillation frequency recorded in the abovementioned storage means. In this case, calibration can be performed in regard to the variation in time of the capacitor's capacitance.

Also, the present Application's method for controlling a device for judging the type of liquid inside a container is a method for controlling a device, which is for judging the type of liquid inside a container and comprises: a plate capacitor, having two plate electrodes positioned in opposing manner; a container supporting means, holding, in a region besides the region sandwiched by the abovementioned two plate electrodes, a non-conductive container that can contain a liquid in the interior thereof; a means for detecting the capacitance of the abovementioned capacitor or the oscillation frequency of an oscillation circuit containing the abovementioned capacitor; and a sensor, detecting whether or not the abovementioned container is positioned on the abovementioned container supporting means; and comprises: a first detection step of detecting that the abovementioned container is not positioned on the abovementioned container supporting means; a first measurement step, wherein, given the detection of the abovementioned first detection step, the capacitance of the abovementioned capacitor or the oscillation frequency of the abovementioned oscillation circuit is measured; a second detection step of detecting that the abovementioned container is positioned on the abovementioned container supporting means; a second measurement step, wherein, given the detection of the abovementioned second detection step, the capacitance of the abovementioned capacitor or the oscillation frequency of the abovementioned oscillation circuit is measured; and a step of notifying whether or not the difference between the capacitance or oscillation frequency measured in the abovementioned first measurement step and the capacitance or oscillation frequency measured in the abovementioned second measurement step is greater than a predetermined threshold value. By having such an arrangement, a measurement can be executed and a judgment, for example, of whether or not the liquid in a container is safe (is a liquid having water as a main component) can be made at the instant the container is positioned.

The above-described method may further comprise: a third measurement step of measuring the capacitance of the abovementioned capacitor or the oscillation frequency of the abovementioned oscillation circuit after the elapse of a predetermined time after the abovementioned first measurement step; and a step, wherein, if the absolute value of the difference between the capacitance or oscillation frequency measured in the abovementioned first measurement step and the capacitance or oscillation frequency measured in the abovementioned third measurement step is greater than a predetermined value, the abovementioned first measurement step and the abovementioned third measurement step are repeated, and if the absolute value of the abovementioned difference is not greater than the predetermined value, the detection of the abovementioned container being positioned on the abovementioned container supporting means is awaited and the steps from the abovementioned first measurement step onward are repeated after the elapse of a predetermined time. In this case, calibration can be executed automatically when the measurement of a liquid inside a container is not being performed.

A block diagram showing an example of the arrangement of a device for judging the type of liquid in a container, which is an embodiment of this invention.

FIG. 2

A flowchart for explaining an example of a method of judging a liquid inside a container by the device for judging the type of liquid inside a container, which is an embodiment of this invention.

FIG. 3

Enlarged views of a container supporting member 3 and a container 2.

FIG. 4

A graph showing the changes of oscillation frequency measured for containers of various shapes by this embodiment's device.

FIG. 5

A graph showing the changes of oscillation frequency for the case where the distance from the capacitor to a container is fixed regardless of the type of container.

FIG. 6

A diagram showing another example of a container supporting member and containers.

FIG. 7

A diagram showing another example of a container supporting member and containers.

FIG. 8

Diagrams showing another example of a container supporting member and containers.

FIG. 9

A diagram showing another example of a container supporting member and containers.

FIG. 10

A diagram showing another example of a container supporting member and containers.

FIG. 11

A diagram showing another example of a container supporting member and containers.

FIG. 12

A block diagram showing an example of the arrangement of a device for judging the type of liquid in a container, which is another embodiment of this invention.

FIG. 13

A diagram showing a third electrode part of Embodiment 2 in an enlarged manner.

FIG. 14

Graphs showing an example of data that demonstrate an effect of this Embodiment 2.

FIG. 15

Graphs showing another example of data that demonstrate an effect of this Embodiment 2.

FIG. 16

A diagram showing another example of a third electrode of Embodiment 2.

FIG. 17

A diagram showing another example of a third electrode of Embodiment 2.

FIG. 18

A diagram showing another example of a third electrode of Embodiment 2.

FIG. 19

A diagram showing another example of a third electrode of Embodiment 2.

BEST MODE FOR CARRYING OUT THE INVENTION

Embodiments of this invention shall now be described in detail based on the drawings.

Embodiment 1

Figure 1:
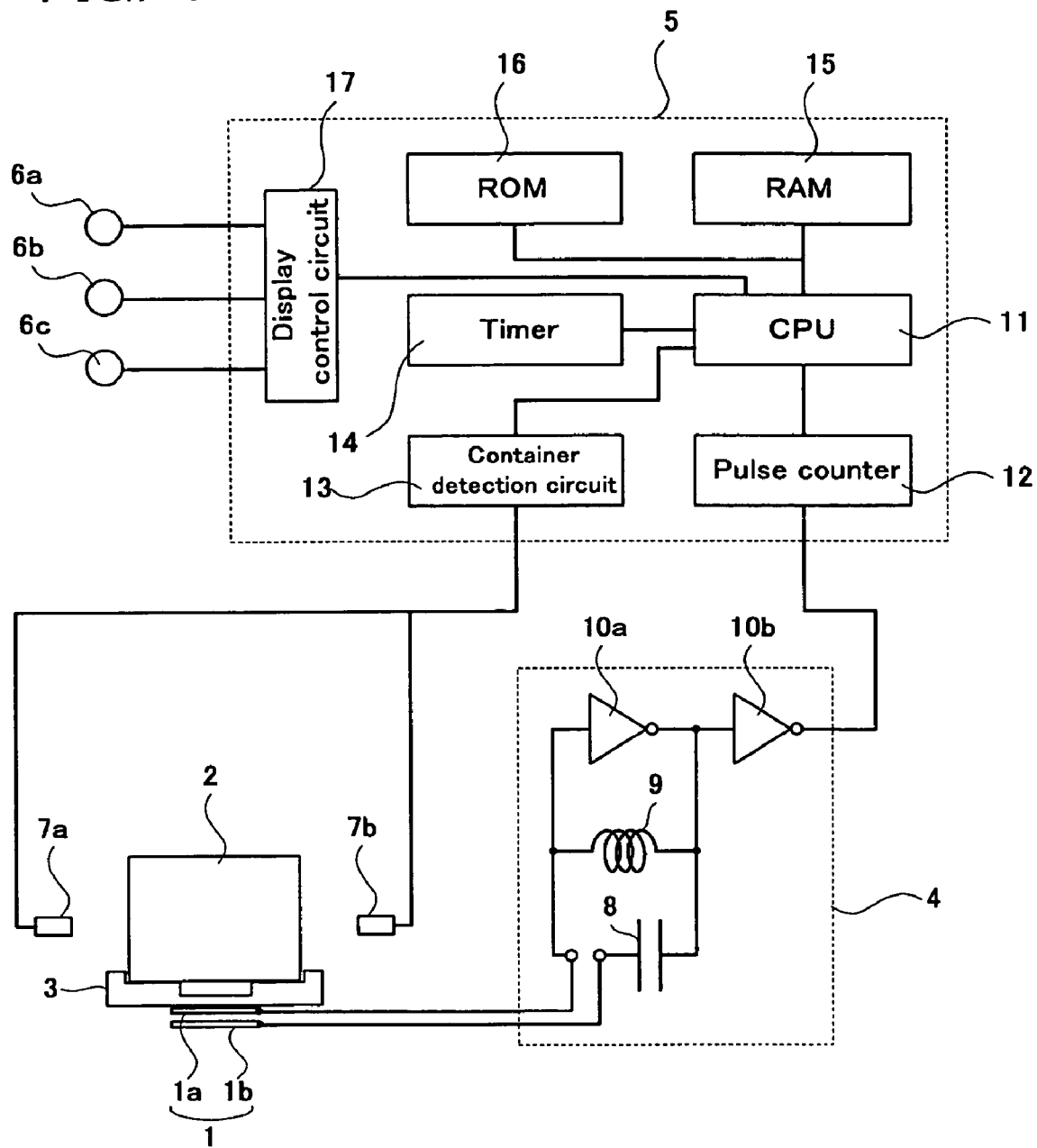
FIG. 1

FIG. 1 is a block diagram showing an example of the arrangement of a device for judging the type of liquid in a container, which is an embodiment of this invention. This embodiment's device for judging the type of liquid in a container has a capacitor 1, a container supporting member 3, which holds a container 2, an oscillation circuit 4, a control part 5, LED display devices 6a, 6b, and 6c, and container sensors 7a and 7b. Oscillation circuit 4 comprises capacitor 1, a capacitor 8, a coil 9, and NOT circuits 10a and 10b, and control part 5 includes a CPU (central processing unit) 11, a pulse counter 12, a container detection circuit 13, a timer 14, a RAM (random access memory) 15, a ROM (read-only memory) 16, and a display control circuit 17.

Capacitor 1 is a plate capacitor having two plate electrodes 1a and 1b disposed in parallel. The material of the plate electrodes is not restricted in particular as long as it is conductive. The size of each of plate electrodes 1a and 1b is, for example, 5 cm×12 cm, and the electrode interval is, for example, 5 mm. Between the electrodes, there may be nothing inserted (that is, a state where air exists) or a plastic or other material of low dielectric constant may be inserted. Though a parallel plate capacitor 1, with which plate electrodes 1a and 1b are disposed in parallel is used as an example here, there is no particular need for plate electrodes 1a and 1b to be disposed in parallel.

Container 2 is, for example, a PET bottle that is a container of a commercially sold drink. The container may also be one that is formed of another material, such as a glass bottle. However, container 2 must be formed of a non-conductive material and is preferably a dielectric body of low dielectric constant. Though a container with a rectangular column shape is used as an example here, the container may have a cylindrical column shape or spherical shape as shall be described later. A liquid to be subject to inspection is contained in the interior of the container.

Container supporting member 3 is a member that supports container 2 according to its size. Container supporting member 3 must be formed of a non-conductive material and is preferably a dielectric body of low dielectric constant. Container supporting member 3 shall be described in detail later. Though with the present embodiment, an example, wherein container 2 is positioned on top of container supporting member 3 and capacitor 1 is positioned below container supporting member 3, is described, the up, down, left, and right positional relationships are not restricted in particular as long as there is a mechanism that pushes container 2 against container supporting member 3.

Oscillation circuit 4 is an oscillation circuit, with which the oscillation frequency changes when the capacitance of capacitor 1 changes. The oscillation circuit oscillates substantially at a resonance frequency that is determined by the capacitances of capacitor 1 and capacitor 8 and the inductance of coil 9. The oscillation is output in the form of a pulse voltage by means of NOT circuits 10a and 10b, and the oscillation frequency is determined from the number of pulses counted within a predetermined time (for example, 1 second) by pulse counter 12.

Control part 5 controls this embodiment's device for judging the type of liquid in a container. CPU 11 is a general-purpose processing device and can execute processes in accordance with a predetermined program. Pulse counter 12 is controlled by CPU 11 and counts the pulses that are output from oscillation circuit 4. Container detection circuit 13 controls container sensors 7a and 7b and detects that container 2 is positioned or is not positioned on container supporting member 3. Timer 14 is controlled by CPU 11 and is used to measure the elapse of time. RAM 15 is a temporary storage device for data. It holds a program and data loaded from ROM 16 and secures the work area to be used in executing the program. The program and data used in this device are recorded in ROM 16. A hard disk drive or other memory device may be used in place of ROM 16. Display control circuit 17 controls the display of LED display devices 6a, 6b, and 6c.

LED display devices 6a, 6b, and 6c display the state of the present device and the results of measurement of the type of liquid in container 2 by this device as shall be described later. For example, LED display device 6a is green, LED display device 6b is blue, and LED display device 6c is red. Though an example where the state and measurement result of the device are notified (displayed) by LED display devices 6a, 6b, and 6c shall be described here, any other suitable notification means may be applied instead. For example, notification by the display of a message by a liquid crystal display device, the sounding of a buzzer upon detection of abnormality, etc., may be applied.

Container sensors 7a and 7b are sensors for detecting that container 2 is positioned on container supporting member 3. An optical sensor having sensor 7a as a light emitting part and sensor 7b as a light receiving part can be cited as an example. A proximity sensor or other type of sensor may also be used instead.

Figure 2:
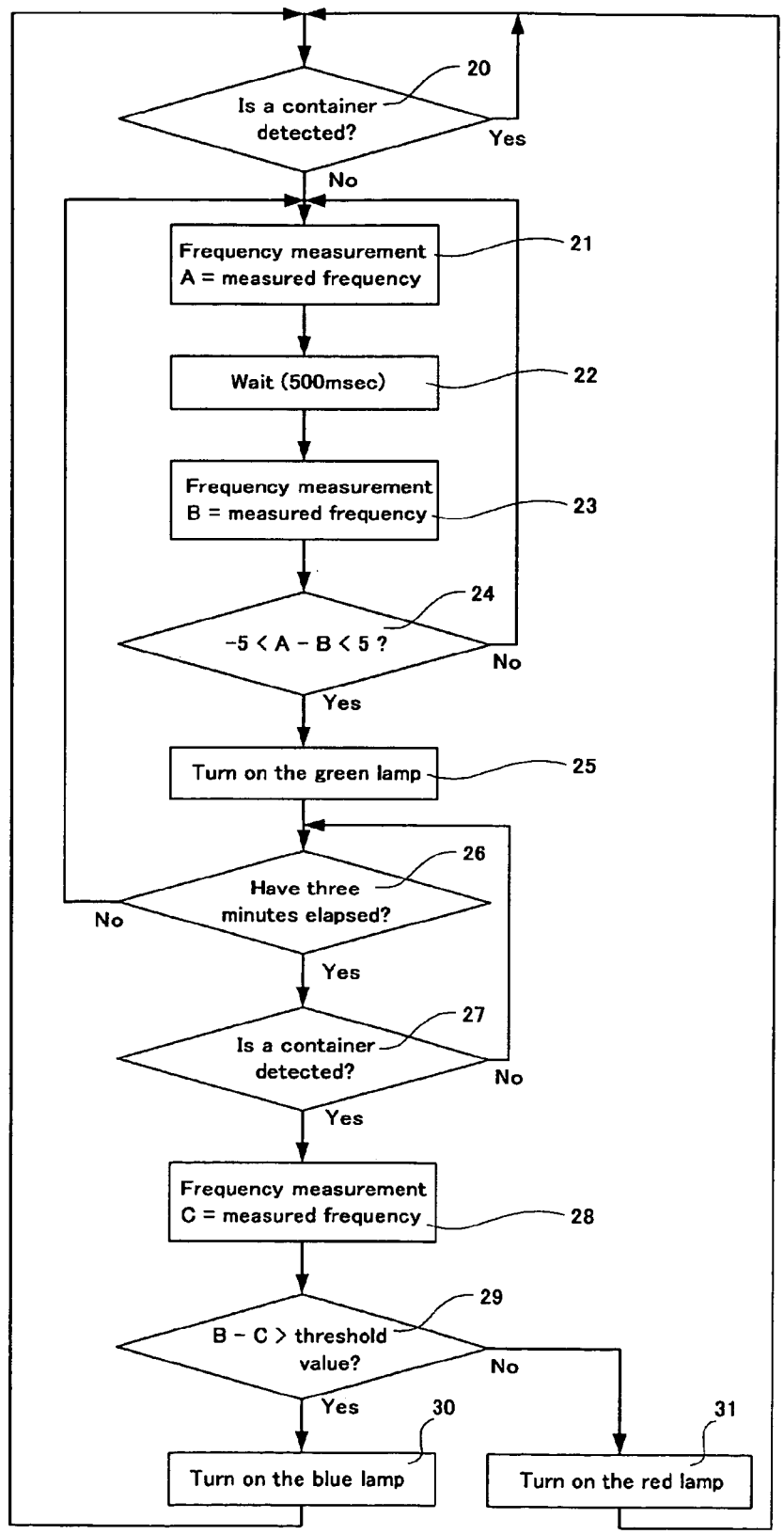

FIG. 2 is a flowchart for explaining an example of a method of judging a liquid inside a container by this embodiment's device for judging the type of liquid inside a container. With regard to the processes that shall be described below, the procedures thereof can be realized by a computer program, and this program is recorded in the abovementioned ROM 16. With this Description, a program shall be deemed as comprising a part of this invention's device as long as it is recorded in ROM 16 or other storage device. Also, though in the following description, an example of executing the processes described below by means of a computer program shall be described, obviously the same process may be realized by a control means using sequence control, automatic control by hardware, etc.

First in step 20, whether or not a container 2 is detected is judged. If a container is detected here, step 20 is repeated until a container is not detected. If a container is not detected, step 21 is entered.

In step 21, a frequency measurement is executed. For the frequency measurement, a suitable period, such as one second, etc., is determined, and the number of pulses counted by pulse counter 12 within this period is measured. The oscillation frequency can be determined by determining the number of pulses counted per second from the measured value. The oscillation frequency that is measured here is recorded as variable A in, for example, RAM 15.

Next, waiting is carried out, for example, for 0.5 seconds (step 22) and then the oscillation frequency is measured again (step 23). The measured oscillation frequency is recorded as variable B. The difference between the recorded A and B is then determined (A–B), and it is judged whether or not the absolute value thereof is greater than a predetermined value, for example, 5 Hz (step 24). If the difference is greater than the predetermined value, it is judged that the device is not stable, a return to step 21 is carried out, and the same processes are repeated.

If the difference is judged to be less than the predetermined value in step 24, it is judged that the device is stable and the green lamp is lit (step 25). By confirming that the green lamp is lit, an operator of the device can recognize that this device can be used.

At the same time as the lighting of the green lamp, the timer is activated and whether or not, for example, three minutes have elapsed is judged (step 26). If three minutes have elapsed, the processes from step 21 are repeated to judge whether or not the device is stable. If it is judged in step 26 that three minutes have not elapsed, step 27 is entered and the processes of detecting and measuring a container is entered. Though here, three minutes is given as an example of the elapsed time, this is just an example. The period in which the stability of the device can be checked is simply set to three minutes, and this time may be set suitably in accordance with the stability of the device.

In step 27, it is judged whether or not a container is detected, and if a container is not detected, step 26 is returned to and the above process is repeated. If a container is detected, the oscillation frequency is measured and the measurement result is recorded as variable C (step 28).

The difference between variable B and variable C is then determined and it is judged whether the difference value is greater or smaller than a predetermined threshold value (step 29). That is as mentioned above, the value of variable B is the oscillation frequency when a container is not set, and the value of variable C is the value of the oscillation frequency when a container is set. If some form of liquid is contained inside the container, since the dielectric constant of a liquid is greater than that of air, the value of C will be less than B. Meanwhile, if the container contains a liquid having water as a main component, since water has a high dielectric constant than that of gasoline or other hazardous liquid, the capacitance of capacitor 1 will be large, the oscillation frequency will be low, and thus the value of B–C will be large. Oppositely, if gasoline or other hazardous liquid is contained in the container, the capacitance of capacitor 1 will be small in comparison to the above case and the value of B–C will thus be small. The threshold value is set as a value by which these cases can be distinguished.

Consequently, if in step 29, B–C is found to be greater than the threshold value, it can be judged that the liquid inside the container is a safe liquid that has water as a main component and the blue lamp is lit (step 30). Oppositely, if B–C is not greater than the threshold value in step 29, since it cannot be judged that the liquid inside the container is a safe liquid that has water as a main component, the red lamp, which indicates an abnormal state, is lit (step 31). After steps 30 and 31, a return to step 20 is carried out and the above-described processes are repeated. The type of liquid inside the container can thus be judged.

Figure 3:
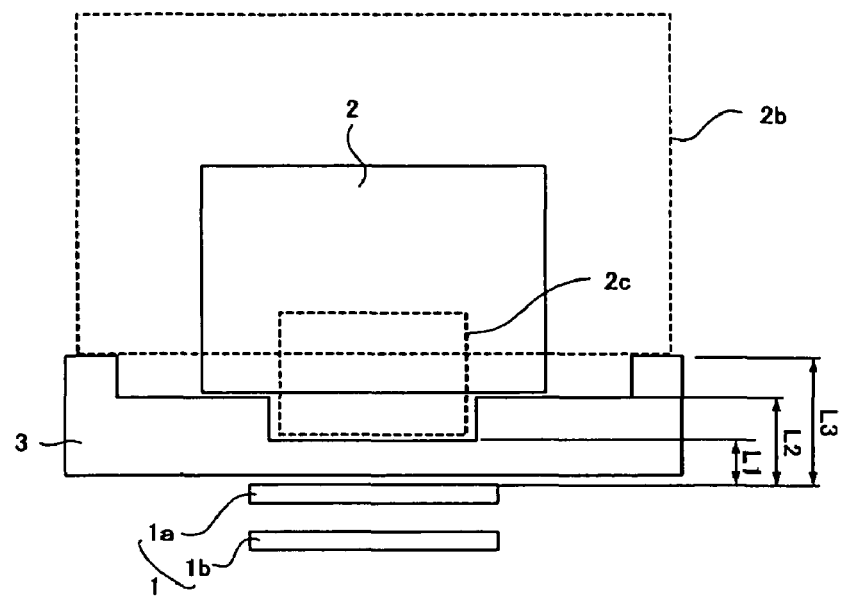
Figure 3:
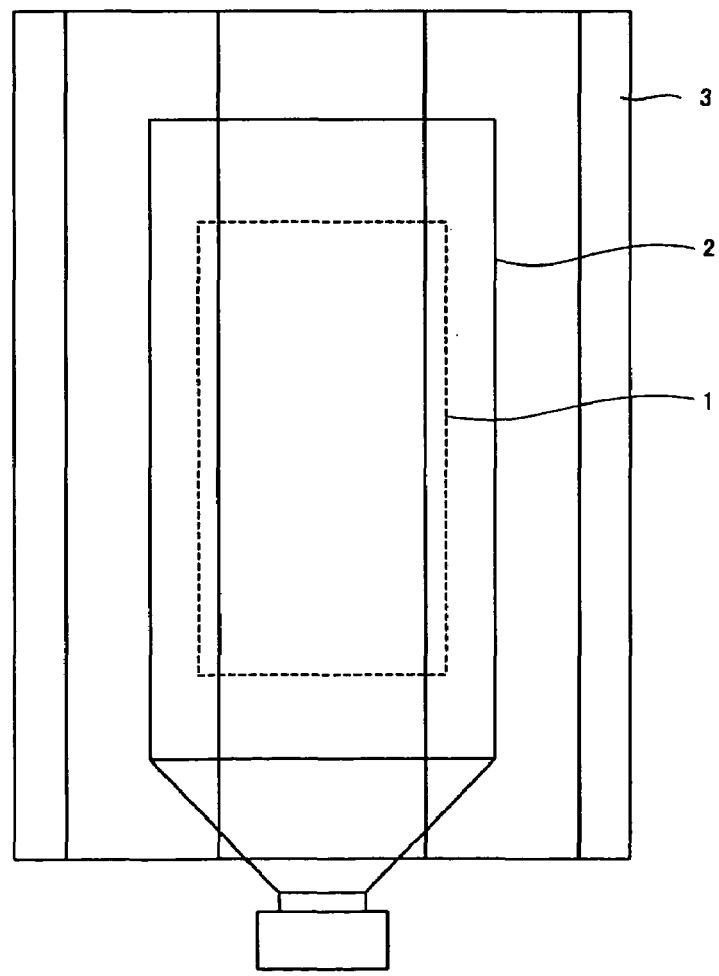

FIG. 3 shows enlarged views of container supporting member 3 and a container 2. The upper diagram is a front view and the lower diagram is a top view. As shown in the upper diagram of FIG. 3, container supporting member 3 has stairs-like members positioned so as to oppose each other and is arranged so that a small container 2c will be positioned on the lowest step, container 2 will be positioned on the middle step, and a large container 2b will be positioned on the top step. That is, the distance from plate electrode 1a is arranged to be L1, L2, and L3, respectively, in accordance with the size of the container. Since container supporting member 3 is thus arranged so that the distance from capacitor 1 becomes greater the greater the size of a container, the electric flux lines due to the leakage electric field from capacitor 1 can be fixed substantially and not depend on the size of the container. This means that the type of liquid inside a container can be judged without dependence on the size of the container. Also, since container supporting member 3 (container 2) is positioned at the exterior of capacitor 1, the leakage electric field of capacitor 1 is used for measurement. Since the leakage electric field is stronger the closer to capacitor 1, the contribution to a change of capacitance is greater at a lower part of a container and relatively weaker at an upper part of the container. Thus even if the remaining amount of a liquid in a container is no more than half, etc., since the liquid will stay at a lower part, the liquid will be measured. Measurement that does not depend on the remaining amount of liquid in a container is thus enabled.

Figure 4:
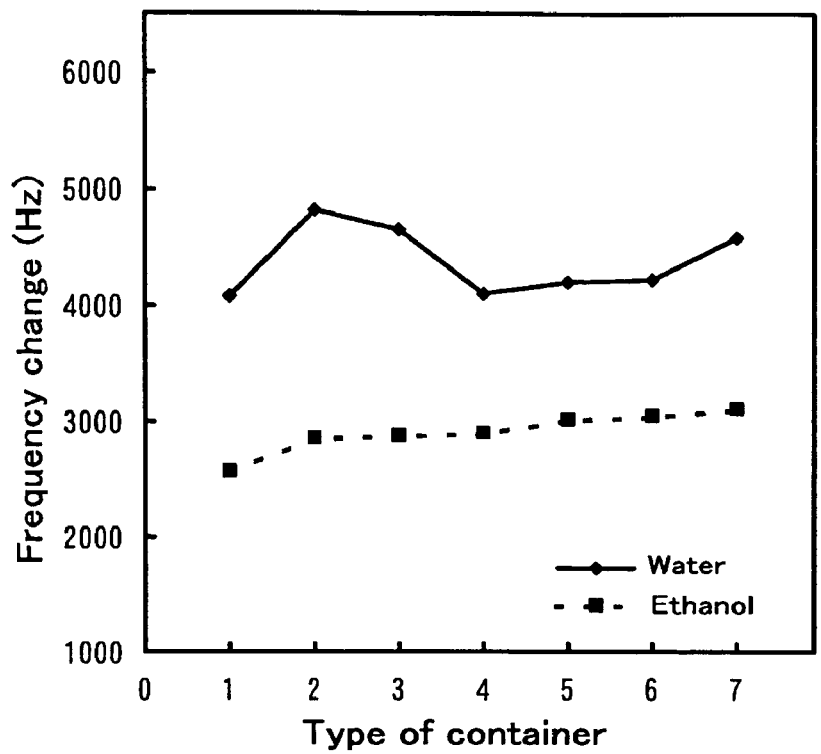
Figure 5:
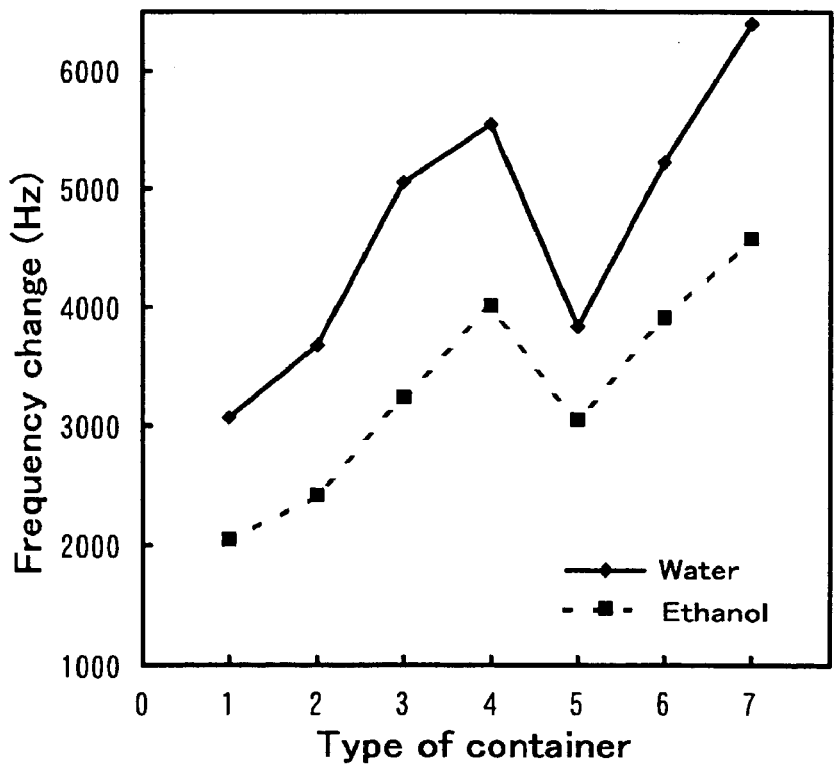

FIG. 4 is a graph showing the changes of oscillation frequency measured for containers of various shapes by this embodiment's device. FIG. 5 is a diagram for comparison and is a graph showing the changes of oscillation frequency for the case where the distance from the capacitor to a container is fixed regardless of the type of container. In FIG. 4 and FIG. 5, the ordinate axis indicates the frequency change and the abscissa axis indicates the difference of container. On the abscissa axis, 1 indicates a 350-milliliter cylindrical column container, 2 indicates a 500-milliliter cylindrical column container, 3 indicates a 500-milliliter rectangular column container, 4 indicates a 900-milliliter rectangular column container, 5 indicates a 1500-milliliter cylindrical column container, 6 indicates a 1500-milliliter rectangular column container, and 7 indicates a 2000-milliliter rectangular column container. The solid line indicates cases where water is contained in the containers and the broken line indicates cases where ethanol is contained in the containers. With each container, the liquid is filled substantially to the maximum capacity.

As shown in FIG. 4 and FIG. 5, with any of the containers, when a comparison is made with the same container, the frequency change is larger in the case where water is contained than in the case where ethanol is contained. This reflects the difference in the dielectric constants of the contents. However, as shown in FIG. 5, the frequency change in the case where ethanol is filled in the container of 7 (2000-milliliter rectangular column container) is greater than in the case where water is filled in the container of 5 (1500-milliliter cylindrical column container). This indicates that in cases where these containers are filled with water or ethanol, the contents cannot be judged with a single threshold value. However, with the present embodiment shown in FIG. 4, since the distance from the capacitor is changed according to the size of a container, the frequency change for the container of 7 (2000-milliliter rectangular column container) can be made small by positioning the container further away. The distance according to the size of container is adjusted so that the frequency change when filled with ethanol will be substantially the same for the other containers as well. This can be achieved substantially by setting the width of the first step (with the distance from the bottom side thereof to the capacitor being L1) to 30 mm, the width of the second step (with the distance from the bottom side thereof to the capacitor being L2) to 55 mm, and thereby setting L1=8 mm, L2=13 mm, and L3=16 mm. As a result, the frequency changes in cases where the respective containers are filled with ethanol are substantially fixed at 3000 Hz as shown in FIG. 4, thus enabling judgment of whether or not the content of each container is water by using a single threshold value (for example, 3500 Hz).

As described above, by using this embodiment's device, the type of liquid in a container (whether or not the liquid has water as a main component) can be judged without dependence on the shape of the container and the remaining amount of liquid in the container.

Figure 6:
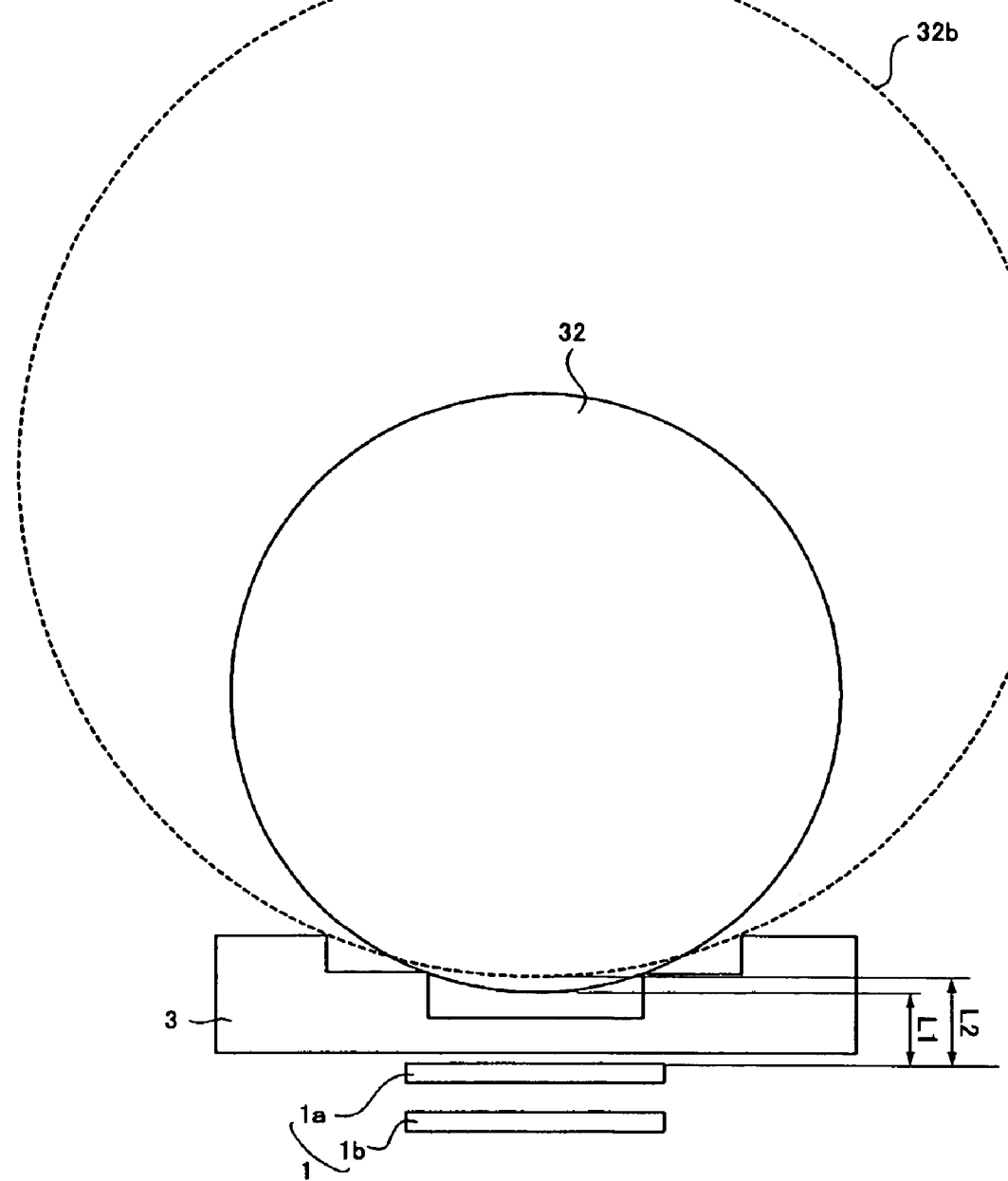

Though in the above-described example, a rectangular column shape is used as an example of the outer shape of a container, the outer shape may be a cylindrical column shape as shown in FIG. 6. Even in this case, the height of a container can be adjusted in accordance with the outer shape of the container.

Figure 7:
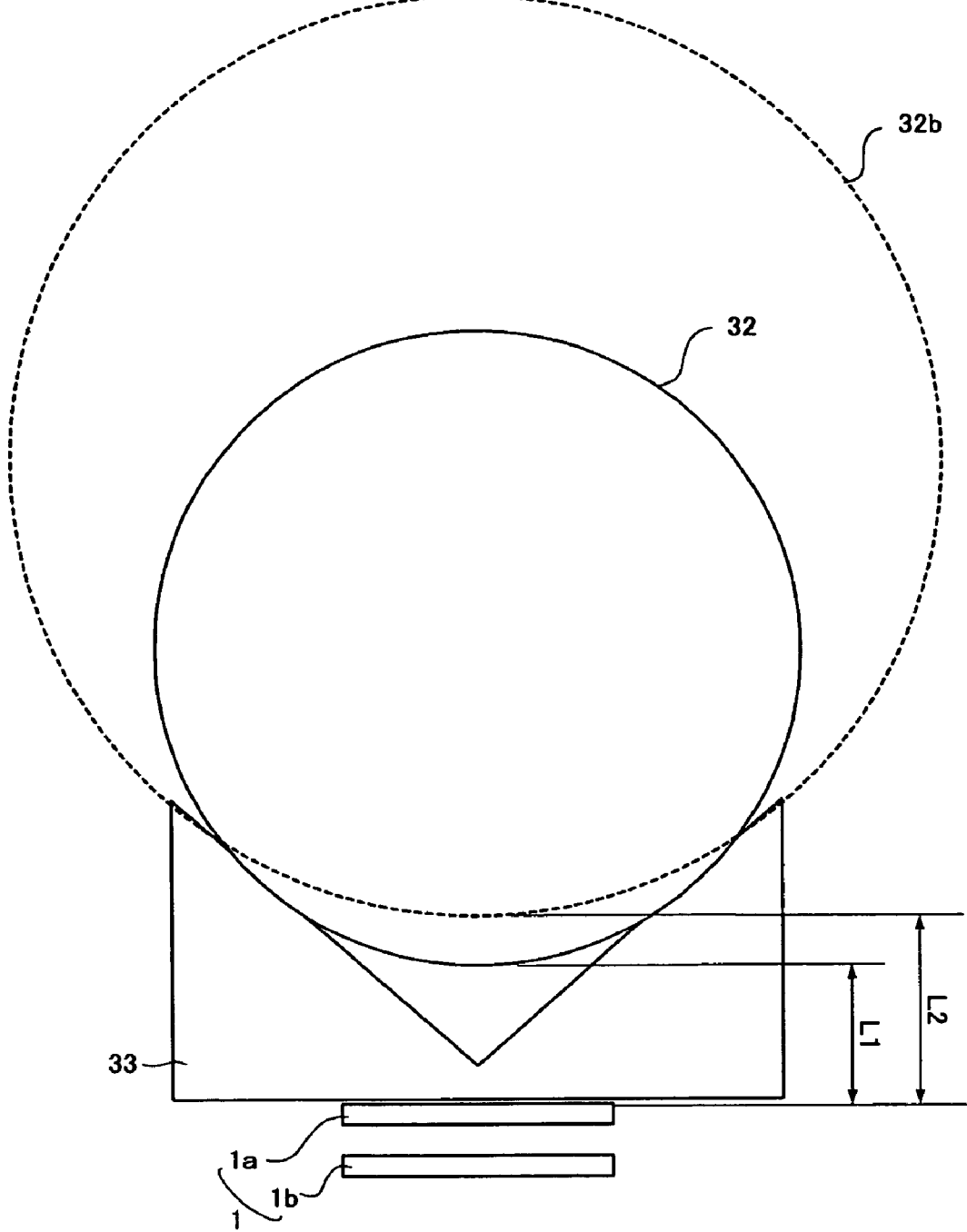

Also, though with the above-described example, a member having stairs-like parts is used as an example of the container supporting member, the member may instead have a V-shaped cross section as shown in FIG. 7. The height of a container can be adjusted according to its size in this case as well.

Figure 8:
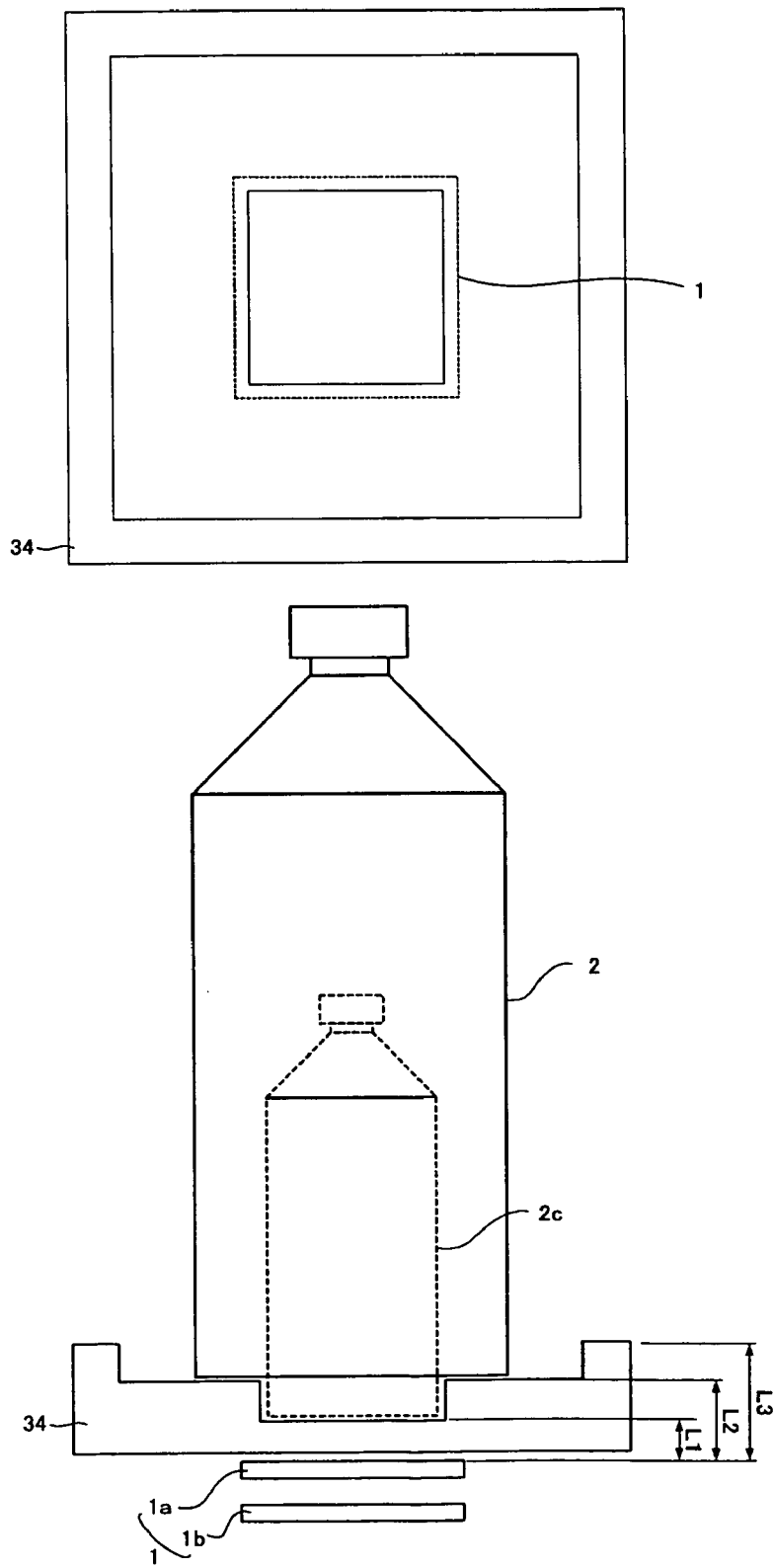

Also, though with the above-described example, an example of measuring with a container set down on its side was described, a measurement may be made with a container being set upright as shown in FIG. 8. In this case, an arrangement having stairs-like members that surround a bottom part of a container as illustrated may be cited as an example of a container supporting member 34. Needless to say, a container of a cylindrical column shape or spherical shape can be used with the arrangement of FIG. 8. Also in place of container supporting member 34, a member having a conical opening may be applied. The cross section of a member having a conical opening profile is the same as that shown in FIG. 7, and it can thus be readily understood that the height of a container can be adjusted according to its size in this case as well.

Figure 9:
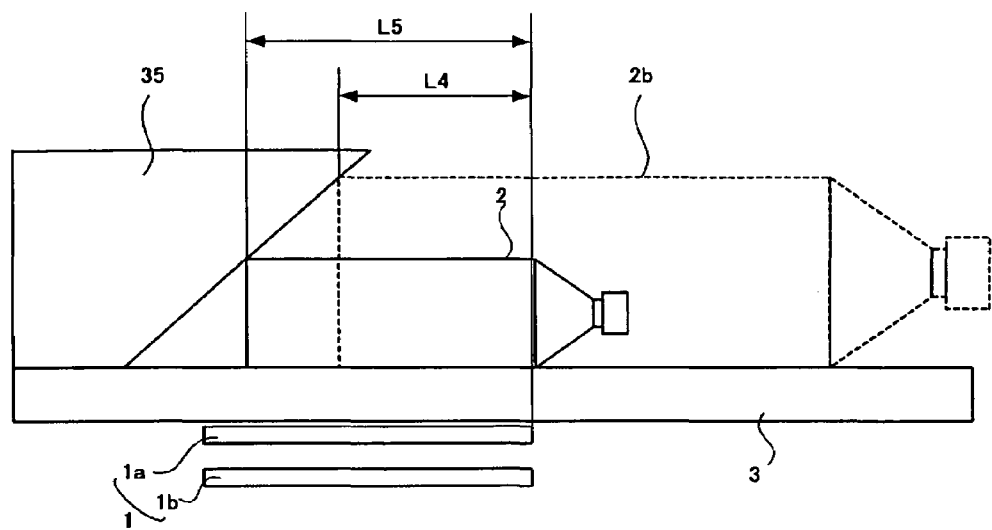

Also, with the above-described examples, methods of adjusting the perpendicular distance from capacitor 1 according to the size of a container were described as examples for making the number of electric flux lines, crossing a liquid inside the container, substantially fixed. However, as shown in FIG. 9, the distances L4 and L5, of overlap of containers with capacitor 1 as viewed from above, may be adjusted according to container size instead. In this case, the adjustment can be realized by a container supporting member 35 having an inclined surface that is inclined in the direction in which a container is set.

Figure 10:
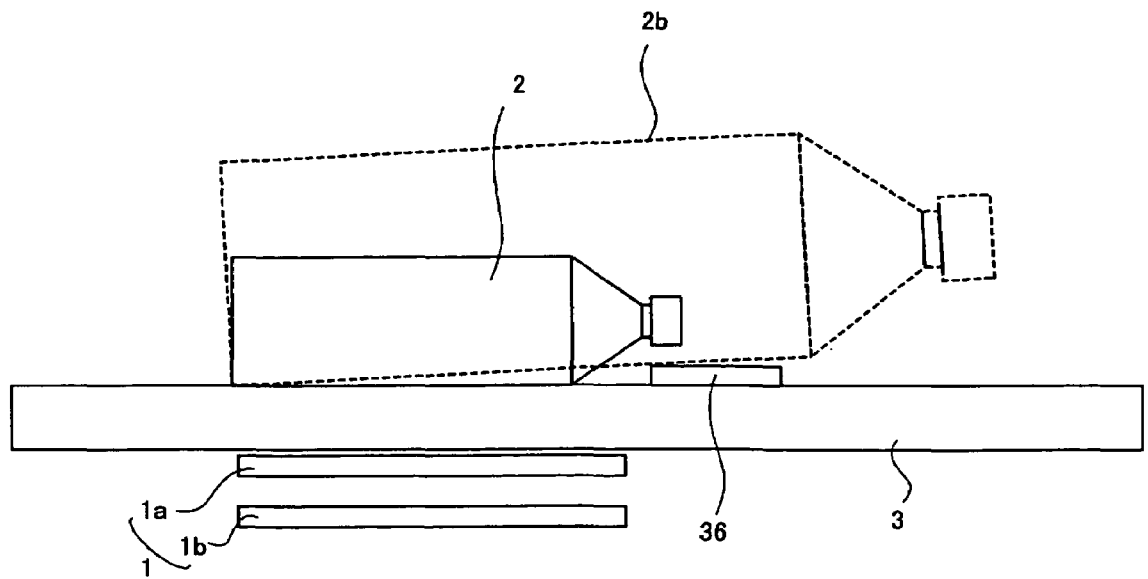

Also as shown in FIG. 10, a step member 36 may be used as a step of a stairs-like member. In this case, a container 2b, of a size such that a part thereof will be set on step member 36, is raised by step member 36 and thus made large in the average distance from capacitor 1. The same effects as those described above can thus be provided.

Figure 11:
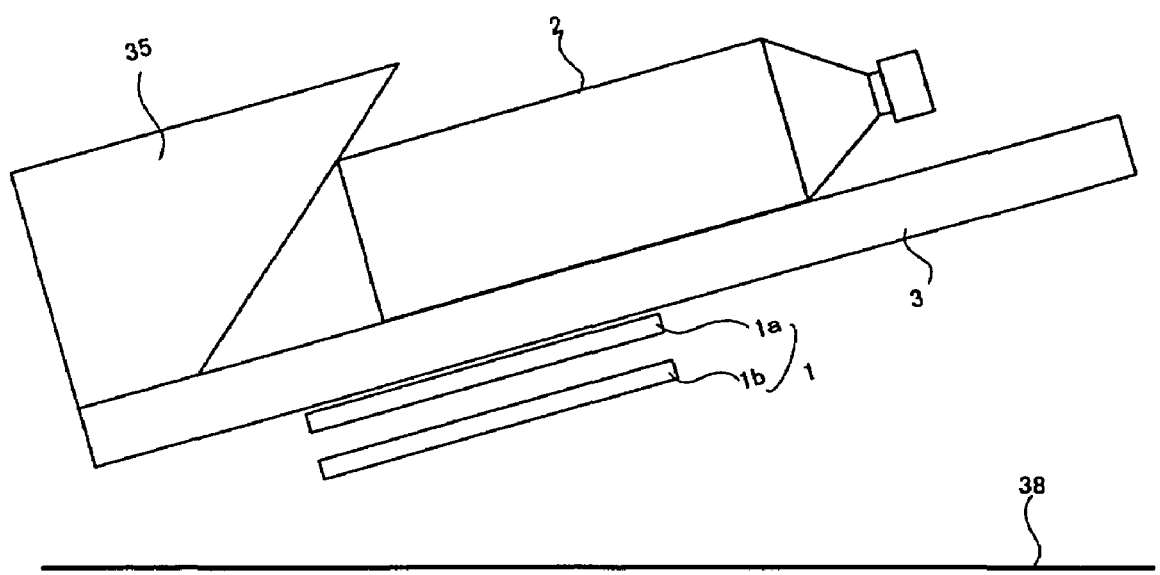

Also as shown in FIG. 11, container supporting means 3 and 35 may be inclined at a predetermined angle with respect to a level surface 38 with the relative position of container 2 and first plate electrode 1a being maintained as shown in FIG. 11. Since in this case, the liquid collects at a lower part of container 2, an effect is provided for the judgment of the type of liquid in cases where the liquid amount is low.

Embodiment 2

Figure 12:
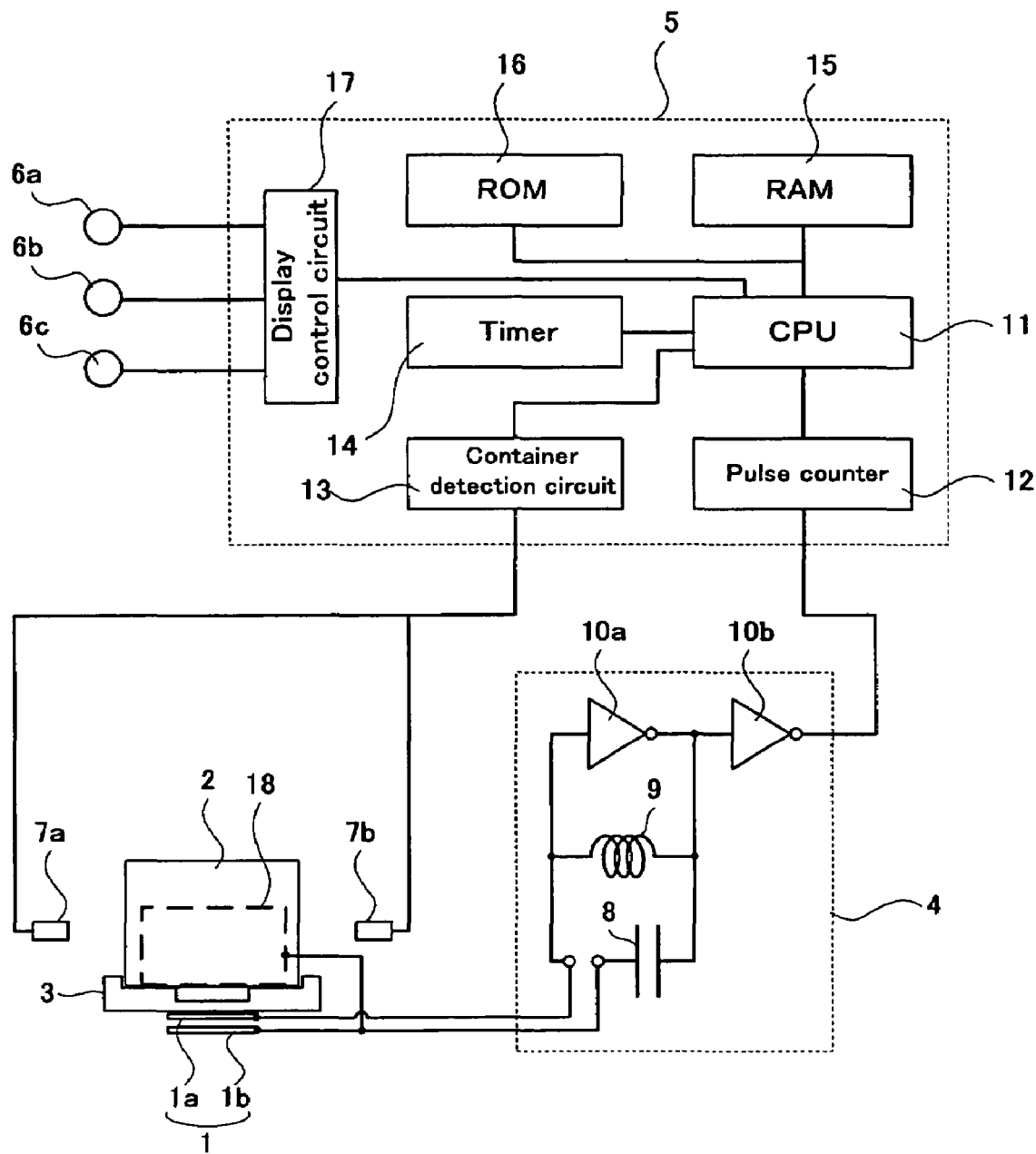

FIG. 12 is a block diagram showing an example of the arrangement of a device for judging the type of liquid in a container, which is another embodiment of this invention. Besides having a third electrode 18, this device for judging the type of liquid of Embodiment 2 is the same as Embodiment 1 described above and redundant description shall be omitted. The method of judging the type of liquid using this device of Embodiment 2 is the same as that of Embodiment 1 described above.

Figure 13:
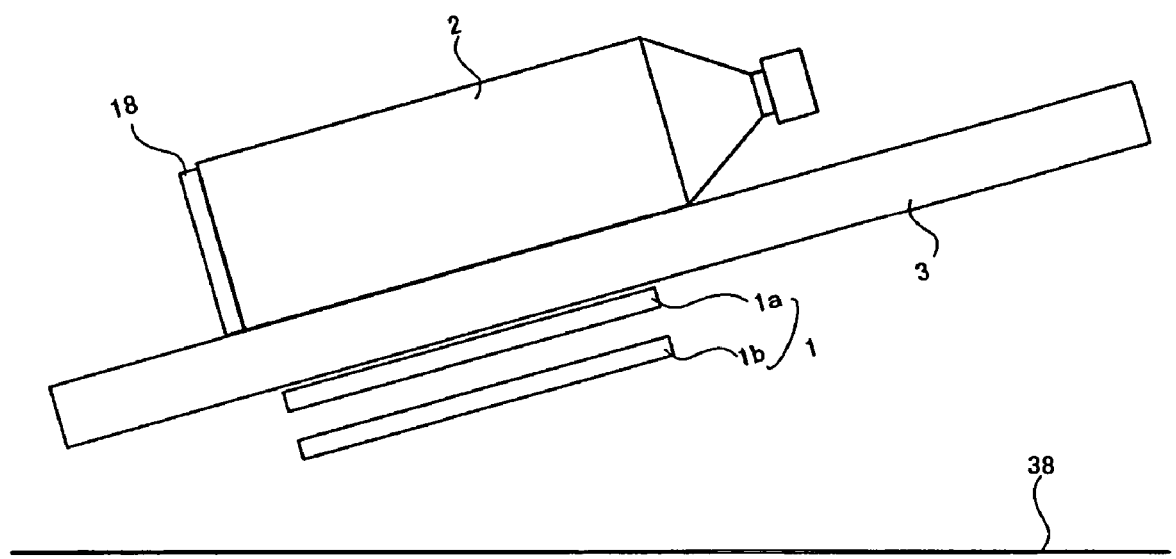

As mentioned above, the device of Embodiment 2 has a third electrode 18. As shown in FIG. 13, third electrode 18 is positioned to be in contact with a bottom part of a container 2. Third electrode 18 is also connected to one plate electrode 1b of capacitor 1, and the electric potential thereof is kept the same as the electric potential of plate electrode 1b. The electric potential of plate electrode 1b is generally the ground potential. Though an example where the electric potential of third electrode 18 is the ground potential shall be described here, the electric potential of third electrode may be arbitrary as long as the voltage differs from the other plate electrode 1a of capacitor 1. Here, that the voltage differs means that the amplitude differs, the phase differs, or both the amplitude and phase differ with respect to an AC voltage applied to plate electrode 1a.

By positioning such a third electrode 18, which is maintained at an electric potential that differs from the voltage applied to plate electrode 1a, to be in contact with the bottom surface of container 2, the leakage electric field from capacitor 1 is drawn in the direction of third electrode 18 and the density of the electric flux passing through the liquid inside container 2 becomes large in comparison to the case where third electrode 18 is not disposed. This means that the change of capacitance of capacitor 1, which reflects the difference in dielectric constant of the liquid inside the container, becomes large, and consequently the precision of judgment of the liquid inside the container is improved.

Figure 14:
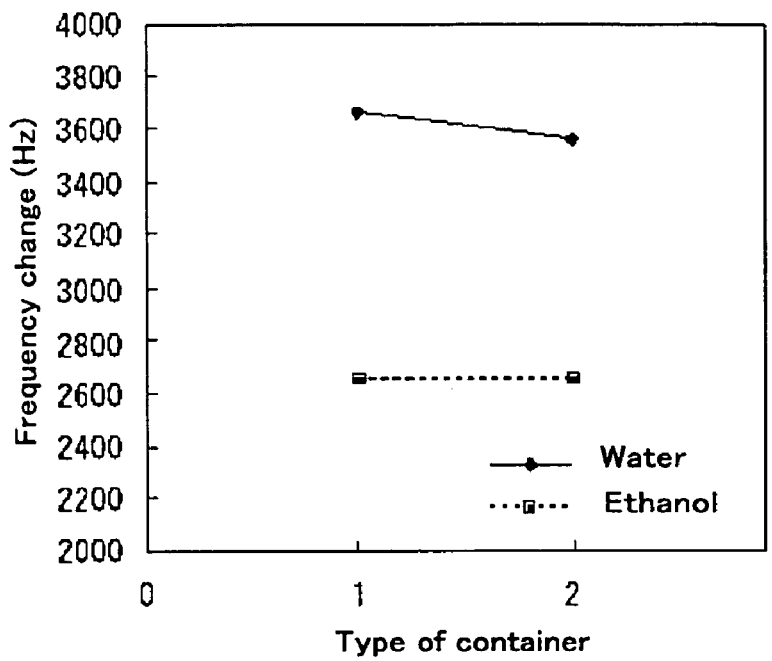
Figure 14:
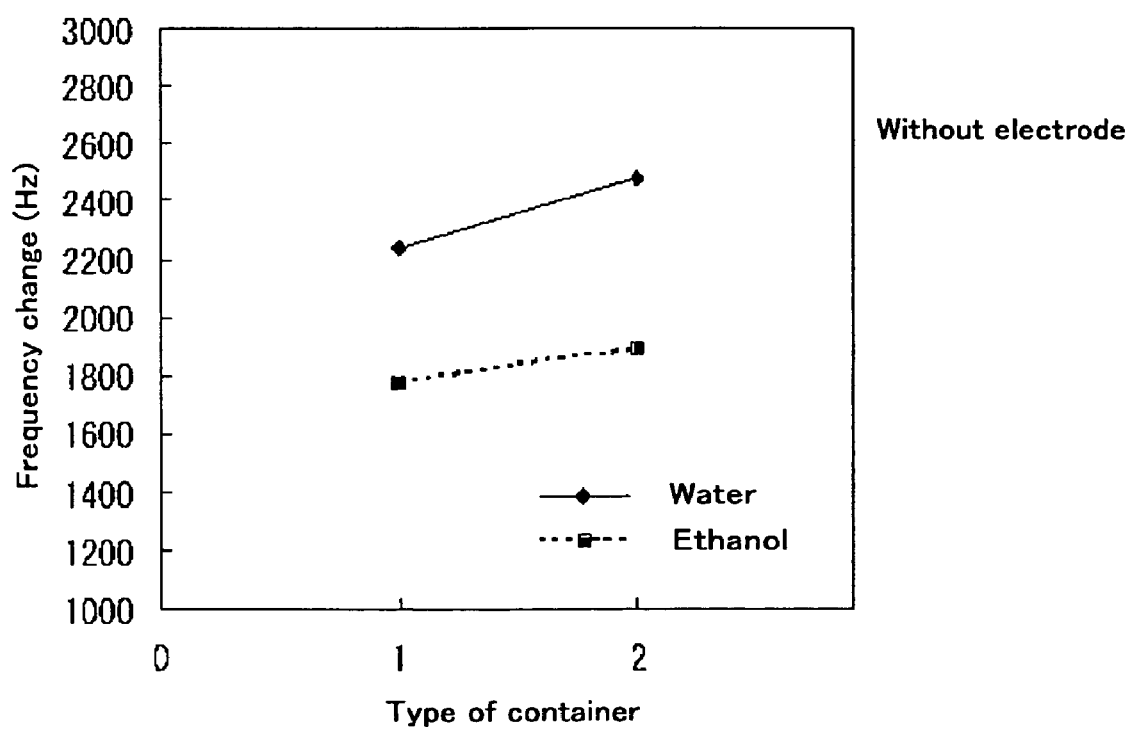

FIG. 14 shows graphs of an example of data that demonstrate an effect of this Embodiment 2. The upper diagram shows the change of resonance frequency (frequency change) when third electrode 18 is disposed and the lower diagram shows the change of resonance frequency when third electrode 18 is not disposed. In FIG. 14, container type 1 is a 900 ml PET bottle and type 2 is a 1500 ml PET bottle. The results of cases where the respective containers are filled to substantially the maximum capacity with water or ethanol are shown.

The shapes, positioning, etc., of capacitor 1 and container supporting member 3 are the same as those of Embodiment 1.

The results of FIG. 14 show that whereas when third electrode 18 is not provided, the difference of the resonance frequency changes of water and ethanol is approximately 500 Hz, when third electrode 18 is provided, the difference of the resonance frequency changes reaches 1 kHz, that is, the difference of the frequency changes is approximately doubled. The results thus indicate though the type of liquid in the interior of a container can be judged with a single threshold value in both cases, when third electrode 18 is provided, the detection allowance is large and an adequate SN ratio can be secured even if there is noise.

Figure 15:
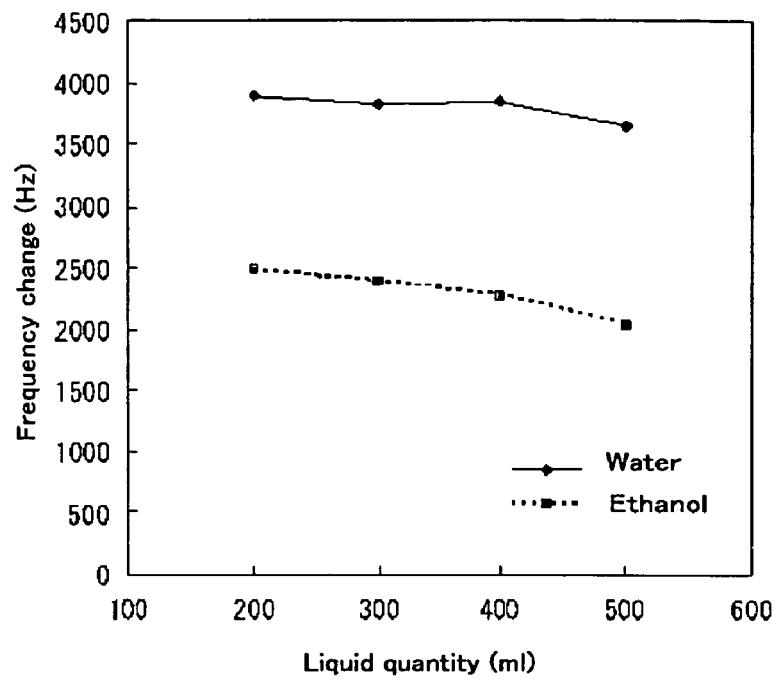
Figure 15:
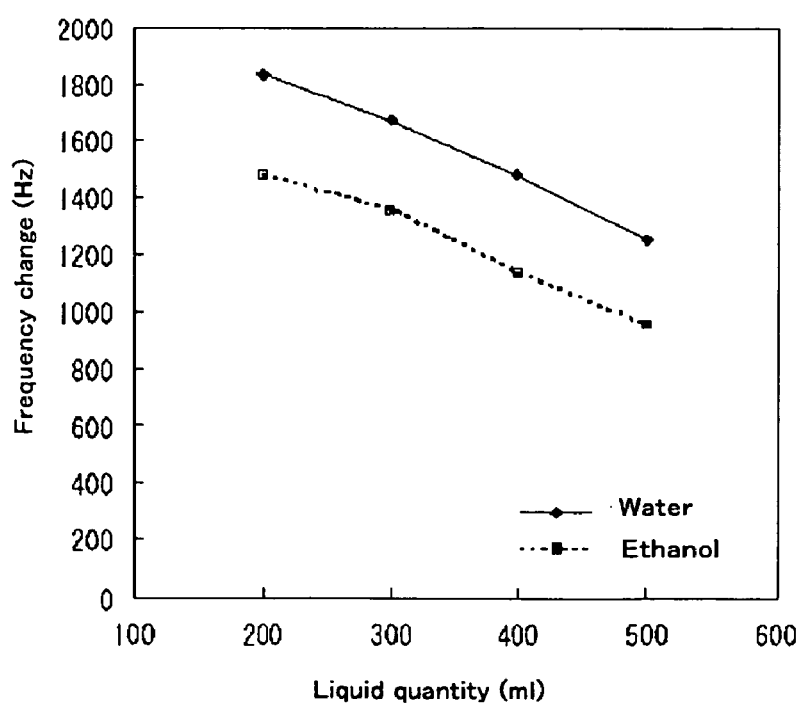

FIG. 15 shows graphs of another set of data that demonstrate an effect of this Embodiment 2. The upper diagram shows the change of resonance frequency (frequency change) when third electrode 18 is disposed and the lower diagram shows the change of resonance frequency when third electrode 18 is not disposed. In FIG. 15, the liquid amount indicates states in which the remaining liquid amount in a 500 ml PET bottle are varied. In the case where third electrode 18 is not disposed (lower diagram of FIG. 15), when the remaining liquid amount in the 500 ml PET bottle is varied between 200 ml and 500 ml, the resonance frequency changes greatly depending on the liquid amount. The frequency change for the case where there is 200 ml of ethanol thus becomes higher than the frequency change for the case where there is 500 ml of water, and it is no longer possible to judge the type of liquid with a single threshold value. Meanwhile, in the case where third electrode 18 is disposed (upper diagram of FIG. 15), the resonance frequency does not vary greatly even with a variation of the liquid amount. As a result, even when the liquid amount changes from 200 ml to 500 ml in a case where the container is a 500 ml PET bottle, the type of liquid in the interior of the container can be judged with a single threshold value (for example, 3700 Hz). The device of this Embodiment 2, which is provided with third electrode 18, thus exhibits a significant effect in cases where the remaining amount of liquid in a container varies.

For this Embodiment 2, a case where third electrode 18 is put in contact with an outer wall (bottom part) of a container was described as an example. However, third electrode 18 does not necessarily have to be put in contact with the outer wall of a container and may instead be disposed at a position away from the container. According to examinations by the present inventor, the effect of disposing third electrode 18 can be obtained under the above-described measurement conditions of FIG. 14 and FIG. 15 as long as the distance from the outer wall of the container is less than 20 mm.

Figure 16:
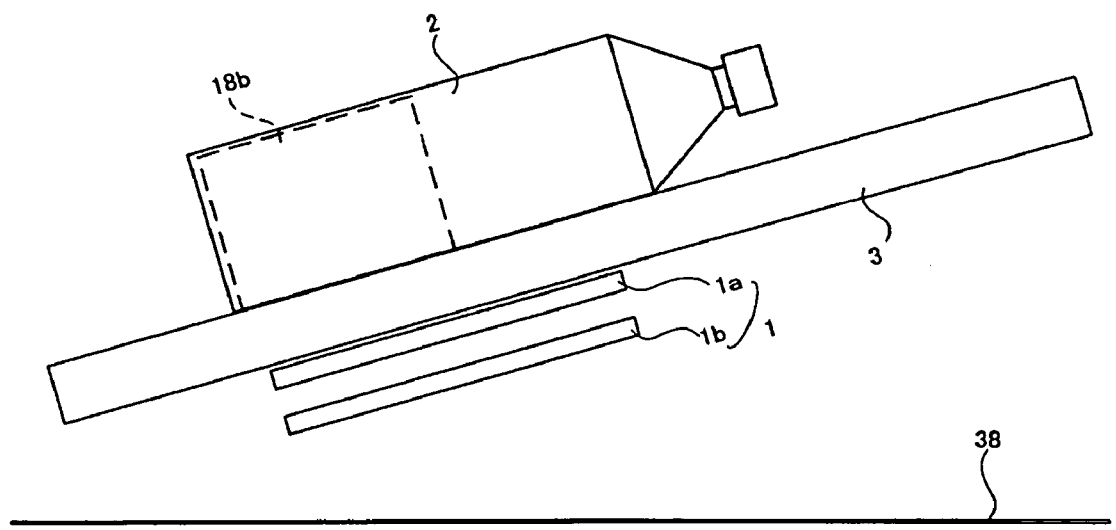
Figure 17:
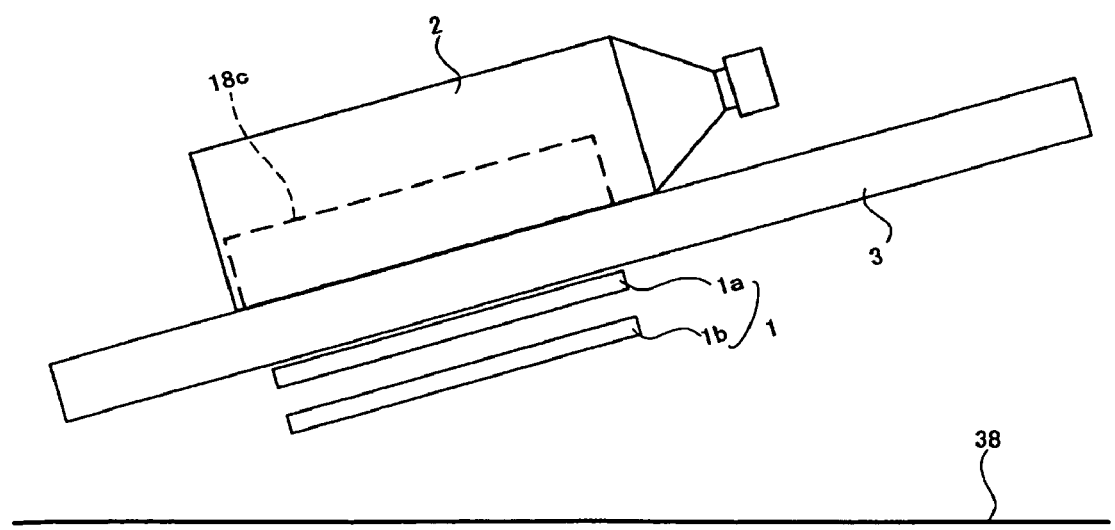

Also, though with this Embodiment 2, a case where third electrode 18 is disposed at a bottom part of a container was described, a third electrode 18b may instead be disposed at the bottom surface side of a side wall of a container as shown in FIG. 16 or a third electrode 18c may be disposed at a lower side of a side wall of a container as shown in FIG. 17. That is, it is sufficient that, even when the amount of liquid remaining in the interior of container 2 is low, the liquid be retained at a lower side due to gravity and third electrode 18, 18b, or 18c be disposed at the vicinity of this retained liquid. By positioning the third electrode so that it is set along the liquid that is retained in the above manner, the electric flux that is attracted by the third electrode can be made to pass through the liquid inside the container effectively to enable observation of the capacitance change of capacitor 1 (resonance frequency change of the resonance circuit) according to liquid type.

Figure 18:
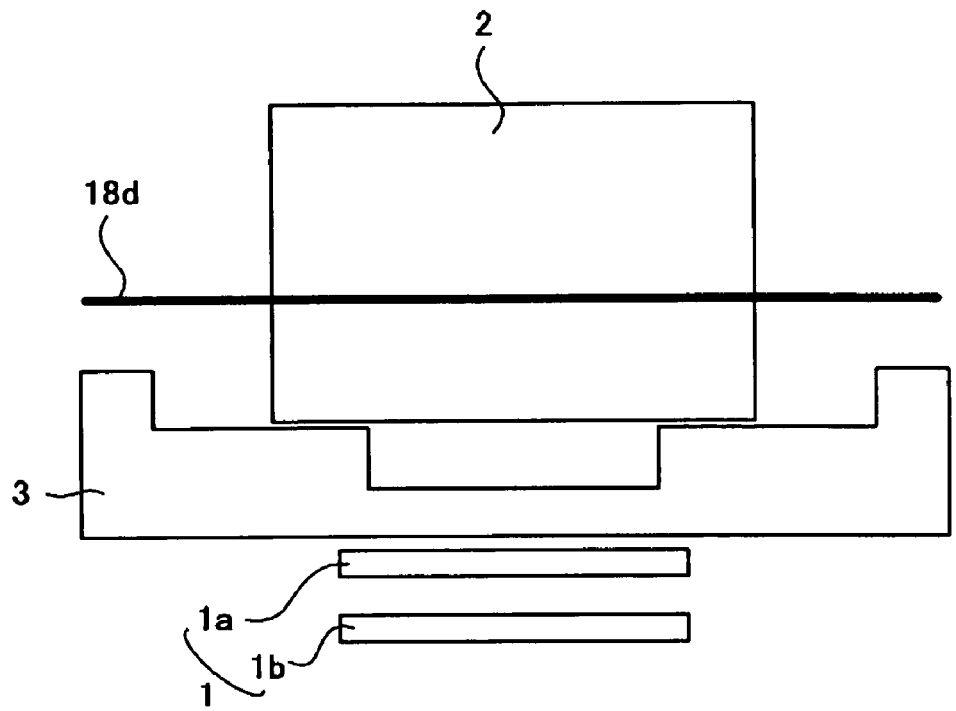

Also, though with this Embodiment 2, a plate electrode is used as an example of the third electrode, the shape of this electrode is not limited to a plate shape. That is, a linear electrical wire may be used as a third electrode 18d as shown in FIG. 18, and the wire does not have to be a single wire but may be a plurality of wires. Also, the wire does not have to be straight and may be curved arbitrarily as long as it is disposed along or near a wall surface of container 2.

Figure 19:
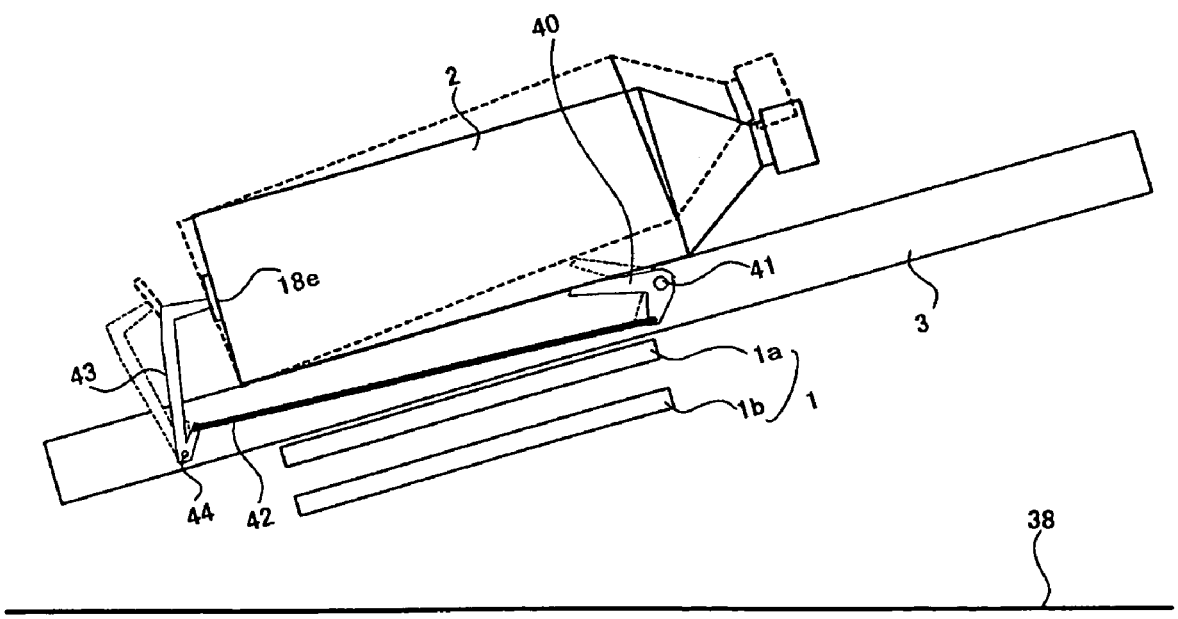

Also, with this Embodiment 2, fixed electrodes are used as examples of third electrode 18, etc. However, the third electrode does not have to be fixed and may be a movable electrode. For example, as shown in FIG. 19, container supporting member 3 may be equipped with a rotor 40, which rotates in accordance with a supporting point 41, and a rotor 43, which rotates in accordance with a link 42 and a supporting point 44, and a third electrode 18e may be equipped at a tip of rotor 43. Rotor 40 and rotor 43 are connected by link 42, and are maintained in the state indicated by the dotted lines by an unillustrated spring or other resilient member when a container 2 is not positioned on container supporting member 3. And when a container 2 is positioned, rotor 40 is pushed down by the weight of the container itself and, by motion via link 42, rotor 43 is put in the state indicated by the solid lines, that is, third electrode 18e is put in the state in which it is pressed against the bottom surface of container 2. By thus arranging third electrode 18e to be movable, third electrode 18e is positioned appropriately so as to contact an outer wall of container 2 even when the size or shape of container 2 changes. Though an arrangement in which third electrode 18e is made movable by a link mechanism was described here, obviously a mechanism, wherein the positioning of container 2 is detected by a photoelectric switch, etc., and third electrode 18e is driven by a motor, etc., given this detection, maybe employed instead.

Also, though with this Embodiment 2, a rectangular column shape is used as the outer shape of a container, the embodiment can obviously be applied to containers of other shapes that were indicated as examples for Embodiment 1.

Though this invention has been described specifically above, this invention is not limited to the above described embodiments and various modifications are obviously possible within a range that does not fall outside the gist of this invention. For example, though in the above-described examples, the change of capacitance of capacitor 1 is detected by means of oscillation circuit 4, detection by direct measurement of the capacitance of capacitor 1 is also possible.

EFFECTS OF THE INVENTION

By the invention of the present Application, a device and a judging method for judging the type of liquid inside a container, which can be applied to containers of various shapes and can be applied to cases where the remaining amounts of liquids in containers differ, can be provided. In particular, a device can be provided that can judge the type of liquid with good sensitivity even when the remaining amount of the liquid in a container is low.

INDUSTRIAL FIELD OF APPLICATION

This invention relates to a device for judging the type of liquid inside a container and a control method for the same and is particularly effective in application to an art of judging whether or not a liquid inside a container is a non-hazardous liquid having water as a main component.

What is claimed is:

1. A device for judging the type of liquid inside a container, comprising:
    a plate capacitor comprising two plate electrodes disposed opposite to each other;
    a container supporting means for holding, in a region other than the region sandwiched by said two plate electrodes, a non-conductive container that can contain a liquid; and
    a third electrode, besides said two plate electrodes, that is an electrode outside said container and that is disposed along a portion of said container at which said liquid inside said container is retained due to gravity,
    wherein the type of liquid inside the container is judged by detecting the capacitance of said capacitor or the oscillation frequency of an oscillation circuit containing said capacitor.

2. The device for judging the type of liquid inside a container according to claim 1, wherein said third electrode is a plate electrode or a line electrode that is disposed along a surface that is a flat surface perpendicular to said plate capacitor and that is in contact with an outer side of said container.

3. The device for judging the type of liquid inside a container according to claim 2, wherein said third electrode is moved to an outer surface of said container upon detection of said container being disposed on said container supporting means or in linkage with said container being disposed on said container supporting means.

4. The device for judging the type of liquid inside a container according to claim 1, having either:
    a first arrangement wherein a voltage of said third electrode differs in absolute value and/or phase from a voltage of a first plate electrode of said capacitor that is disposed on the container side; or
    a second arrangement wherein a voltage of said third electrode is equal to a voltage of a second plate electrode of said capacitor that is opposite said first plate electrode.

5. The device for judging the type of liquid inside a container according to claim 1, wherein said container supporting means adjusts, in accordance with the size of said container, the distance between a first plate electrode of said two plate electrodes that is disposed on the side of said container and said container.

6. The device for judging the type of liquid inside a container according to claim 5, wherein said container has a cylindrical or rectangular column outer shape and is supported on said container supporting means, with the columnar direction of said cylindrical or rectangular column shape being set parallel to said first plate electrode, and
    said container supporting means comprises two stairs-like members that increase in height in a direction perpendicular to said first plate electrode and that are disposed opposite each other, wherein the distance between said container and said first plate electrode is adjusted according to the size of said container when an outer peripheral surface of said rectangular column or cylindrical container abuts against the steps or edge parts of the steps of said two stairs-like members.

7. The device for judging the type of liquid inside a container according to claim 6, wherein a step member is disposed on one side of said steps that extend in said columnar direction, and
    a container, which is larger than said container that contacts the steps of said two stairs-like members at its outer peripheral surface, is increased in the average distance to said first plate electrode by one end thereof being raised by said step member.

8. The device for judging the type of liquid inside a container according to claim 5, wherein said container has a cylindrical, rectangular column, or spherical outer shape and is supported on said container supporting means, with the columnar direction of said cylindrical or rectangular column shape being set perpendicular to said first plate electrode, and
    said container supporting means is structured such that it is surrounded by stairs-like members that increase in height in a direction perpendicular to said first plate electrode, wherein the distance between said container and said first plate electrode is adjusted according to the size of said container when the bottom surface of said rectangular column or cylindrical container abuts against the steps of the stairs-like members and when the outer peripheral surface of said spherical container abuts against the edge parts of said steps.

9. The device for judging the type of liquid inside a container according to claim 5, wherein said container has a cylindrical or rectangular column outer shape and is supported on said container supporting means, with the columnar direction of said cylindrical or rectangular column shape being set parallel to said first plate electrode, and
    said container supporting means has a groove with V-cross section having an opening in a direction perpendicular to said first plate electrode, wherein the distance between said container and said first plate electrode is adjusted according to the size of said container when an outer peripheral surface of said rectangular column or cylindrical container abuts against the V-grooved surface.

10. The device for judging the type of liquid inside a container according to claim 5,
    wherein said container has a cylindrical, rectangular column, or spherical outer shape and is supported on said container supporting means, with the columnar direction of said cylindrical or rectangular column shape being set perpendicular to said first plate electrode, and
    said container supporting means has a conical opening in a direction perpendicular to said first plate electrode, wherein the distance between said container and said first plate electrode is adjusted according to the size of said container when an edge part of the bottom surface of said rectangular column or cylindrical container, or the outer peripheral surface of said spherical shape container, abuts against the wall surfaces of said conical opening.

11. The device for judging the type of liquid inside a container according to claim 5, wherein said container supporting means is inclined at a predetermined angle with respect to a level surface while the relative positions of said container supporting means and said two plate electrodes are maintained.

12. The device for judging the type of liquid inside a container according to claim 1, wherein said container supporting means adjusts, in accordance with the size of said container, the area of overlap between said container and said plate electrodes as projected in the normal direction perpendicular to a first plate electrode of said two plate electrodes that is disposed on the side of said container.

13. The device for judging the type of liquid inside a container according to claim 12, wherein said container has a cylindrical, rectangular column, or spherical outer shape and is supported on said container supporting means, with the columnar direction of said cylindrical or rectangular column shape being set parallel to said first plate electrode, and
    said container supporting means has an inclined surface of an acute angle with respect to said first plate electrode, wherein said area of overlap between said container and said plate electrodes is adjusted according to the size of said container when an edge part of the bottom surface of said rectangular column or cylindrical container, or the outer peripheral surface of said spherical container, abuts against said inclined surface.

14. The device for judging the type of liquid inside a container according to claim 12, wherein said container has a cylindrical, rectangular column, or spherical outer shape and is supported on said container supporting means, with the columnar direction of said cylindrical or rectangular column shape being set parallel to said first plate electrode, and said container supporting means has a stairs-like member that increases in height in a direction parallel to said first plate electrode, wherein said area of overlap between said container and said plate electrodes is adjusted according to the size of said container when the bottom surface of said rectangular column or cylindrical container abuts against a step of said stairs-like member, and when the outer peripheral surface of said spherical container abuts against an edge part of said step.

15. The device for judging the type of liquid inside a container according to claim 1, further comprising:

a sensor for detecting whether or not said container is disposed on said container supporting means;

means for detecting the amount of change between the capacitance of said capacitor or the oscillation frequency of said oscillation circuit when said container is not disposed on said container supporting means and the capacitance of said capacitor or the oscillation frequency of said oscillation circuit when said container is disposed on said container supporting means; and a notification means for giving notification as to whether or not said change amount is greater than a predetermined threshold value.

16. The device for judging the type of liquid inside a container according to claim 15, further comprising:

a storage means for recording the capacitance of said capacitor or the oscillation frequency of said oscillation circuit when said container is not disposed on said container supporting means; and means for periodically updating said capacitance or oscillation frequency recorded in said storage means.

17. A device for judging the type of liquid inside a container, comprising:

a plate capacitor comprising two plate electrodes disposed opposite to each other; and a container supporting means for holding, in a region other than the region sandwiched by said two plate electrodes, a non-conductive container that can contain a liquid, wherein the type of liquid inside the container is judged by detecting the capacitance of said capacitor or the oscillation frequency of an oscillation circuit containing said capacitor, and wherein said container supporting means adjusts, in accordance with the size of said container, the distance between a first plate electrode of said two plate electrodes that is disposed on the side of said container.

18. A device for judging the type of liquid inside a container, comprising:

a plate capacitor comprising two plate electrodes disposed opposite to each other; and a container supporting means for holding, in a region other than the region sandwiched by said two plate electrodes, a non-conductive container that can contain a liquid, wherein the type of liquid inside the container is judged by detecting the capacitance of said capacitor or the oscillation frequency of an oscillation circuit containing said capacitor, and wherein said container supporting means adjusts, in accordance with the size of said container, the area of overlap between said container and said plate electrodes as projected in the normal direction perpendicular to a first plate electrode of said two plate electrodes that is disposed on the side of said container.

19. A device for judging the type of liquid inside a container, comprising:

a plate capacitor comprising two plate electrodes disposed opposite to each other;

a container supporting means for holding, in a region other than the region sandwiched by said two plate electrodes, a non-conductive container that can contain a liquid;

a sensor for detecting whether or not said container is disposed on said container supporting means;

means for detecting the amount of change between the capacitance of said capacitor or the oscillation frequency of said oscillation circuit when said container is not disposed on said container supporting means and the capacitance of said capacitor or the oscillation frequency of said oscillation circuit when said container is disposed on said container supporting means; and a notification means for giving notification as to whether or not said change amount is greater than a predetermined threshold value, wherein the type of liquid inside the container is judged by detecting the capacitance of said capacitor or the oscillation frequency of an oscillation circuit containing said capacitor.

20. A method for controlling a device for judging the type of liquid inside a container, said device comprising:

a plate capacitor comprising two plate electrodes disposed opposite to each other;

a container supporting means for holding, in a region other than the region sandwiched by said two plate electrodes, a non-conductive container that can contain a liquid;

means for detecting the capacitance of said capacitor or the oscillation frequency of an oscillation circuit containing said capacitor; and a sensor for detecting whether or not said container is disposed on said container supporting means, said method comprising:

a first detection step of detecting that said container is not disposed on said container supporting means;

a first measurement step of measuring the capacitance of said capacitor or the oscillation frequency of said oscillation circuit upon detection in said first detection step;

a second detection step of detecting that said container is disposed on said container supporting means;

a second measurement step of measuring the capacitance of said capacitor or the oscillation frequency of said oscillation circuit upon detection in said second detection step; and a step of giving notification as to whether or not the difference between the capacitance or oscillation frequency measured in said first measurement step and the capacitance or oscillation frequency measured in said second measurement step is greater than a predetermined threshold value.

21. The method for controlling a device for judging the type of liquid inside a container according to claim 20, further comprising:

a third measurement step of measuring the capacitance of said capacitor or the oscillation frequency of said oscillation circuit after a predetermined time elapses following said first measurement step; and a step of repeating said first measurement step and said third measurement step if the absolute value of the difference between the capacitance or oscillation frequency measured in said first measurement step and the capacitance or oscillation frequency measured in said third measurement step is greater than a predetermined value, or repeating, if the absolute value of said difference is not greater than the predetermined value, the steps from said first measurement step after a predetermined time elapses while awaiting the detection of said container being disposed on said container supporting means.

22. A method for controlling a device for judging the type of liquid inside a container, said device comprising:

a plate capacitor comprising two plate electrodes disposed opposite to each other;

a container supporting means for holding, in a region other than the region sandwiched by said two plate electrodes, a non-conductive container that can contain a liquid;

a third electrode other than said two plate electrodes, of which said capacitor is comprised, wherein said third electrode is an electrode outside said container and that is disposed along a portion of said container at which said liquid inside said container is retained due to gravity;

means for detecting the capacitance of said capacitor or the oscillation frequency of an oscillation circuit containing said capacitor; and a sensor for detecting whether or not said container is disposed on said container supporting means, wherein said device has either a first arrangement wherein the voltage of said third electrode differs in absolute value and/or phase from the voltage of a first plate electrode of said capacitor that is disposed on the side of said container, or a second arrangement wherein the voltage of said third electrode is equal to the voltage of the second plate electrode of said capacitor that is opposite said first plate electrode, said method comprising:

a first detection step of detecting that said container is not disposed on said container supporting means;

a first measurement step of measuring the capacitance of said capacitor or the oscillation frequency of said oscillation circuit upon detection in said first detection step;

a second detection step of detecting that said container is disposed on said container supporting means;

a second measurement step of measuring the capacitance of said capacitor or the oscillation frequency of said oscillation circuit upon detection in said second detection step; and a step of giving notification as to whether or not the difference between the capacitance or oscillation frequency measured in said first measurement step and the capacitance or oscillation frequency measured in said second measurement step is greater than a predetermined threshold value.

* * * * *